United States Patent
Trollope et al.

(10) Patent No.: US 10,167,459 B2
(45) Date of Patent: Jan. 1, 2019

(54) MODIFIED BETA-FRUCTOFURANOSIDASE FOR FRUCTOOLIGOSACCHARIDE PRODUCTION

(71) Applicant: Stellenbosch University, Stellenbosch (ZA)

(72) Inventors: Kim Trollope, Stellenbosch (ZA); Heinrich Volschenk, Stellenbosch (ZA); Johann Ferdinand Gorgens, Stellenbosch (ZA); Gerhardt Coetzee, Strand (ZA)

(73) Assignee: STELLENBOSCH UNIVERSITY, Stellenbosch (ZA)

( * ) Notice: Subject to any disclaimer, the term of this patent is extended or adjusted under 35 U.S.C. 154(b) by 0 days.

(21) Appl. No.: 15/516,372

(22) PCT Filed: Oct. 2, 2015

(86) PCT No.: PCT/IB2015/057554
§ 371 (c)(1),
(2) Date: Mar. 31, 2017

(87) PCT Pub. No.: WO2016/051386
PCT Pub. Date: Apr. 7, 2016

(65) Prior Publication Data
US 2017/0298332 A1  Oct. 19, 2017

(30) Foreign Application Priority Data
Oct. 2, 2014  (ZA) .................... 2014/07138

(51) Int. Cl.
| | |
|---|---|
| *C12N 9/24* | (2006.01) |
| *C12N 9/26* | (2006.01) |
| *A23L 27/30* | (2016.01) |
| *A23L 33/125* | (2016.01) |
| *C12P 19/16* | (2006.01) |

(52) U.S. Cl.
CPC ............ *C12N 9/2431* (2013.01); *A23L 27/33* (2016.08); *A23L 33/125* (2016.08); *C12P 19/16* (2013.01); *C12Y 302/01026* (2013.01); *A23V 2002/00* (2013.01)

(58) Field of Classification Search
CPC .................................................. C12N 9/2431
See application file for complete search history.

(56) References Cited

U.S. PATENT DOCUMENTS

| 6,337,201 B1 | 1/2002 | Yanai et al. |
| 2011/0081449 A1 | 4/2011 | De Leenheer et al. |

FOREIGN PATENT DOCUMENTS

| EP | 0889134 A1 | 1/1999 |
| EP | 1726655 A1 | 11/2006 |

OTHER PUBLICATIONS

De Abreu, M. A., et al., "Screening β-fructofuranosidases Mutant Libraries to Enhance the Transglycosylation Rates of β-(2->6) Fructooligosaccharides," Combinatorial Chemistry & High Throughput Screening, vol. 14, issue 8, Sep. 2011 (accepted Apr. 22, 2011), Benjamin Science Publishers Ltd., pp. 730-738; 9 pages included.
International Search Report dated Jan. 18, 2016 corresponding to International Patent Application No. PCT/162015/057554, filed on Oct. 2, 2015; 3 pages.
Chuankhayan, P., et al., "Crystal Structures of *Aspergillus japonicas* Fructosyltransferase Complex with Donor/Acceptor Substrates Reveal Complete Subsites in the Active Site for Catalysis," Journal of Biological Chemistry, vol. 285, No. 30, Jul. 23, 2010, pp. 23251-23264, 18 pages provided.
Trollope, K. M., et al., "Screen a random mutagenesis library of a fungal β-fructofuranosidase usint FT-MIR ATR spectroscopy and multivariate analysis," Applied Microbiology and Biotechnology, Springer DE, vol. 98, No. 9, Dec. 10, 2013, pp. 4063-4073, 12 pages provided.
Wyk, N. V., et al., "Identification of the gene for β-fructofuranosidase from *Ceratocystis moniliformis* CMW 10134 and characterization of the enzyme expressed in *Saccharomyces cerevisiae*," BMC Biotechnology, Biomed Central Ltd., London GB, vol. 13, No. 1, Nov. 14, 2013, p. 100, 12 pages provided.
Lafraya, A., et al., "Fructo-Oligosaccharide Synthesis by Mutant Versions of *Saccharomyces cerevisiae* Invertase," Applied and Environmental Microbiology, American Society for Microbiology, Sep. 2011, p. 6148-6157, 10 pages provided.
Alvaro-Benito, M., et al., "New Insights into the Fructosyltransferase Activity of Schwanniomyces occidentalis β-Fructofuranosidase, Emerging from Nonconventional Codon Usage and Directed Mutation," Applied and Environmental Microbiology, American Society for Microbiology, Nov. 2010, p. 7491-7499, 9 pages provided.
De Abreu, M. A., et al., "Screening β-fructofuranosidases Mutant Libraries to Enhance the Transglycosylation Rates of β-(2→6) Fructooligosaccharides," Combinatorial Chemistry & High Throughput Screening, vol. 14, issue 8, retrieved online: <http://www.eurekaselect.com/74716/article>, 1 page provided (Abstract only).
De Abreu, M., et al., "Synthesis of 6-Kestose using an Efficient β-Fructofuranosidase Engineered by Directed Evolution," Adv. Synth. Catal. 2013, 355, 1698-1702, Wiley Online Library, Feb. 22, 2013, 5 pages provided.

*Primary Examiner* — Rebecca E Prouty
(74) *Attorney, Agent, or Firm* — Mintz, Levin, Cohn, Ferris, Glovsky and Popeo, P.C.

(57) ABSTRACT

The invention provides variants of the *Aspergillus japonicus* β-fructofuranosidase enzyme which have been modified so as to improve synthesis of inulin-type fructooligosaccharides (FOS) from sucrose. One or more substitutions may be made to the parent β-fructofuranosidase polypeptide at amino acid positions 121, 159, 302 and/or 471 of the mature peptide (SEQ ID NO: 3), corresponding to crystal positions 140, 178, 321 and 490. A method of synthesizing FOS using the variants is also claimed.

20 Claims, 8 Drawing Sheets

Specification includes a Sequence Listing.

---------------------------------------SYHLDTTAPPPTNLSTLPNNTL    41

FHVWRPRAHILPAEGQIGDPCAHYTDPSTGLFHVGFLHDGDGIAGATTANLATYTD    97

TSDNGSFLIQPGGKNDPVAVFDGAVIPVGVNNTPTLLYTSVSFLPIHWSIPYIRG    152

SETQSLAVARDGGRRFDKLDQGPVIADHPFAVDVTAFRDPFVFRSAKLDVLLSLD    207

EEVARNETAVQQAVDGNIEKNAPNYVAVSGGVHGVGPAQFLYRQNGGNASEPQYW    262

EYLGEWWQEATNSSWGDEGTWAGRWGFNFETGNVLFLTEEGHDPQTGEVFVTLGTE    318

GSGLPIVPQVSSIHDMLWAAGEVGVGSEQEGAKVEFSPSMAGFLDNGFSAYAAAG    373

KVLPASSAVSKTSGVEVDRYVSFVWLTGDQYEQADGFPTAQQGWTGSLLLPRELK    428

VQTVENVVDNELVREEGVSWVVGESDNQTARLRTLGITIARETKAALLANGSVTA    483

EELRTLQTAAVVPEAQSPSSKFFVLTAQLEPPASARSSFLQSGFEILASELERTA    538

IYYQFSNESLVVDRSQTSAAAPTNPGLESPTESGKLRLPDVIENGQEQVEPLDLP    593

VVVDNAVVEVYANGRFALSTWARSNYDNSTQIRFFHNGEGEVQFRNVSVSEGLYN    648

ANPERN    654

Fig. 1

MODIFIED BETA-FRUCTOFURANOSIDASE FOR FRUCTOOLIGOSACCHARIDE PRODUCTION

CROSS-REFERENCE TO RELATED APPLICATIONS

This application claims priority to South African provisional patent application number 2014/07138, which is incorporated by reference herein.

FIELD OF THE INVENTION

The invention related to modified β-fructofuranosidases which have improved enzyme activity, in particular fructosyltransferase activity, relative to the parent enzyme.

BACKGROUND TO THE INVENTION

The global demand for fructooligosaccharides (FOS) is growing due to human health benefits associated with their consumption. FOS are prebiotics that selectively stimulate the growth of bifidobacteria, thereby promoting colonic health [1,2]. Further claims as to the effect of FOS consumption relate to mineral absorption, lipid metabolism and the control of type II diabetes and have been extensively reviewed [2-4]. Further to their health benefits, FOS are used in the food industry as low calorie sweeteners. They are also added to food products to improve their organoleptic properties and their inclusion allows producers to label their products as 'functional foods'—a claim that resonates with health conscious consumers [2,3].

It is well known that some β-fructofuranosidases possess the ability to transform sucrose to FOS. β-fructofuranosidases are family 32 glycoside hydrolase (GH32) enzymes that act on sucrose and related β-D-fructofuranosides [5]. They are also known as invertases (EC 3.2.1.26) as they hydrolyse sucrose to produce invert sugar—an equimolar mixture of dextrorotatory D-glucose and levorotatory D-fructose [6]. Crystal structures for GH32 β-fructofuranosidases reveal that the enzymes display a bimodular arrangement of a N-terminal catalytic domain containing a five-bladed β-propeller fold linked to a C-terminal β-sandwich domain [7-10]. β-fructofuranosidases hydrolyse β-glycosidic bonds by a double displacement catalytic mechanism that retains the configuration of the fructose anomeric carbon [11]. Multiple sequence alignments (MSAs) identified a highly conserved aspartate close to the N terminus that serves as the catalytic nucleophile and a glutamate residue that acts as a general acid/base catalyst [12]. The β-fructofuranosidases which are capable of transforming sucrose to FOS possess fructosyltransferase activity whereby the sugar moiety is transferred from the enzyme-fructosyl intermediate to an acceptor other than water [7,13]. This reaction forms the basis of FOS synthesis from sucrose. Enzymes from *Aspergillus* spp. [14-16] and *Aureobasidium pullulans* [17] exhibit good propensities for the synthesis of inulin type FOS from sucrose, with β-(2→1) linkages between fructose units.

Synthesis of FOS ($GF_n$) from sucrose (GF) occurs via a disproportionation reaction with the reaction generalised as $GF_n + GF_n \rightarrow GF_{n-1} + GF_{n+1}$, [18,19]. In a batch reaction the initial products are glucose and 1-kestose (GF2), and as the reaction progresses, nystose (GF3) and β-fructofuranosyl nystose (GF4) levels increase. Reaction conditions influence the dominance of hydrolytic or transferase reactions with high substrate concentrations favouring the latter [14].

Industrial biotransformation of sucrose to FOS is currently conducted in a batch system using the β-fructofuranosidase from *A. niger* ATCC 20611 (subsequently classified as *A. japonicus*). The enzyme is added to a buffered 50-60% (wt/vol) sucrose solution with the reaction proceeding at 50-60° C. for up to 20 hours [19]. These severe industrial conditions impose limitations on activity. The fructosyltransferase activity of the enzyme has been shown to be non-competitively inhibited by the glucose product, limiting complete sucrose conversion [19]. Furthermore, long-term enzyme stability is severely compromised at temperatures above 50° C. despite immobilisation efforts [20].

There is thus still a need for alternative enzymes which are able to efficiently convert sucrose to FOS on an industrial scale.

SUMMARY OF THE INVENTION

According to a first embodiment of the invention, there is provided a modified polypeptide having fructofuranosidase activity, wherein the amino acid sequence of the polypeptide is at least 90% or 95% identical to SEQ ID NO: 3 and has at least one amino acid substitution at position 121, 159, 302 and/or 471 of SEQ ID NO: 3.

The polypeptide may differ only from SEQ ID NO: 3 at one or more of positions 121, 159, 302 and/or 471.

The polypeptide may include a secretion signal peptide at its 5' end, the secretion signal having an amino acid sequence which is at least 90% or 95% identical to SEQ ID NO: 25. The modified polypeptide with secretion signal may have an amino acid sequence which is at least 90% or 95% identical to SEQ ID NO: 26 and which has at least one amino acid substitution at position 154, 192, 335 and/or 504 of SEQ ID NO: 26.

The polypeptide may include any two of the above substitutions, such as at amino acid positions 171 and 302 of SEQ ID NO: 3.

The polypeptide may include any three of the above substitutions, such as at amino acid positions 121, 159 and 302, or at amino acid positions 159, 302 and 471, or at amino acid positions 121, 159 and 471 of SEQ ID NO: 3.

The polypeptide may include any four of the above substitutions, such as at amino acid positions 121, 159, 302 and 471 of SEQ ID NO: 3.

The phenylalanine (F) at amino acid position 154 may be substituted by tyrosine (Y), the alanine (A) at amino acid position 192 may be substituted by proline (P) or serine (S), the glycine (G) at amino acid position 335 may be substituted by asparagine (N), aspartic acid (D), tyrosine (Y) or glutamic acid (E), and/or the glutamine (Q) at amino acid position 504 may be substituted by serine (S), lysine (K) or asparagine (N).

More preferably, the substitution at amino acid position 154 is tyrosine (Y), the substitution at amino acid position 192 is proline (P), the substitution at amino acid position 335 is asparagine (N), and/or the substitution at amino acid position 504 is serine (S).

Even more preferably, the polypeptide may include the following modifications:
F121Y-A159P-G302N-Q471S;
F121Y-A159P-G302N;
A159P-G302N-Q471S;
F121Y-A159P-Q471S; or
A159P-G302N.

Even more preferably, the polypeptide may include the following four modifications: F121Y, A159P, G302N and Q471S.

The polypeptide may comprise an unsubstituted amino acid residue at positions 62, 122, 128, 165, 221, 395 and/or 550 of SEQ ID NO: 3

The polypeptide may comprise an amino acid sequence of any one of SEQ ID NOS: 4-21, such as SEQ ID NO: 4.

The polypeptide may have an improved thermal stability, catalytic rate and lower glucose feedback inhibition levels relative to a polypeptide which has not been modified as described above.

According to a second embodiment of the invention, there is provided a polynucleotide which encodes a modified polypeptide as described above.

The polynucleotide may have a nucleotide sequence which is at least 90% identical to the sequence of nucleotides 100 to 2007 of SEQ ID NO: 1 or SEQ ID NO: 2, or a complement thereof, wherein SEQ ID NO: 1 or SEQ ID NO: 2 has been modified so that the polynucleotide encodes a modified polypeptide as described above.

The polynucleotide may include a $T.$ $reesei$ endoxylanase 2 (xln2) secretion signal. The secretion signal may be encoded by nucleotides 1-99 of SEQ ID NO: 1 or 2.

According to a third embodiment of the invention, there is provided a vector comprising a polynucleotide encoding a modified fructofuranosidase polypeptide as described above.

According to a fourth embodiment of the invention, there is provided a host cell comprising the vector described above.

The host cell may be a microbial cell, such as from a yeast, bacterium or fungus.

According to a fifth embodiment of the invention, there is provided a yeast, fungus or bacterium comprising at least one copy of an exogenous gene coding for a modified polypeptide as described above.

According to a sixth embodiment of the invention, there is provided a process for producing a modified fructofuranosidase polypeptide as described above, the process comprising the steps of transforming a host cell with the polynucleotide described above and causing the polypeptide to be expressed.

The process may also comprise the step of recovering the polypeptide, such as from the transformed host cell or a supernatant into which the polypeptide has been secreted.

The host cell may be a yeast cell, fungal cell or bacterium.

The polypeptide may be expressed under the control of a constitutive or inducible promoter, such as the $S.$ $cerevisiae$ phosphoglycerate kinase 1 (PGK1), glyceraldehyde-3-phosphate dehydrogenase (GAP) promoter or the alcohol oxidase (AOX1) promoter in $Pichia$ $pastoris$.

According to a seventh embodiment of the invention, there is provided a process for producing fructooligosaccharides (FOS), the process comprising the steps of contacting sucrose with a modified polypeptide described above under conditions which cause the sucrose to be converted into fructooligosaccharides. The fructooligosaccharides may be short chain fructooligosaccharides.

The transformed host cell described above may be added to a solution containing sucrose and be caused to express the polypeptide into the solution, or alternatively a purified, partially purified or crude extract of polypeptide may be added directly to the solution containing sucrose.

The fructooligosaccharides may include 1-kestose (GF2), nystose (GF3) and/or β-fructofuranosyl nystose (GF4).

The process may require lower amounts of the modified polypeptide to produce the FOS or may be performed over a shortened reaction time, relative to an unmodified process.

BRIEF DESCRIPTION OF THE FIGURES

FIG. 1: Amino acid sequence of FopA (SEQ ID NO: 3) (numbered according to crystal structure) showing substitutions which were selected for generating a first round of FopA variants.

DETAILED DESCRIPTION OF THE INVENTION

Figure 2:
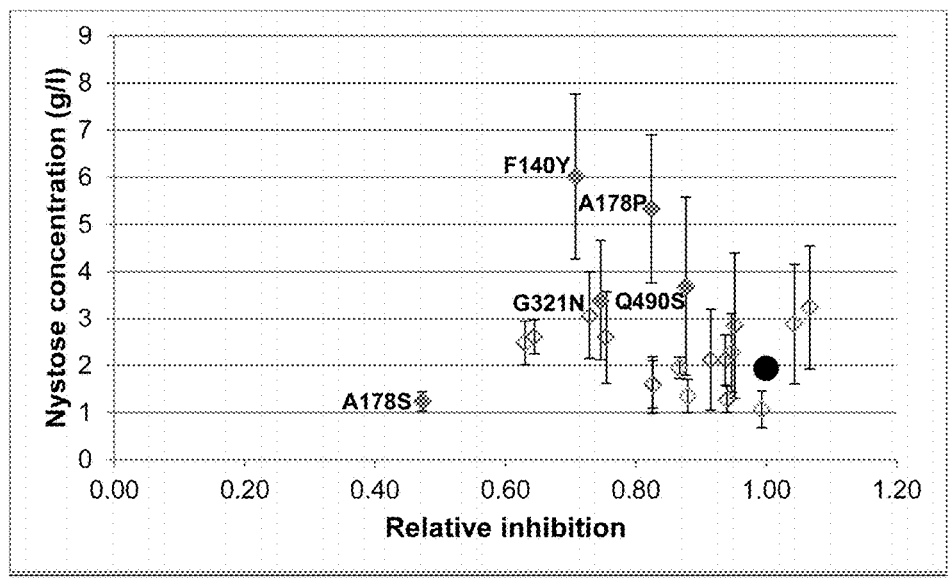
FIG. 2: Screening data for the active first round variants harbouring single amino acid substitutions. The parent enzyme is indicated by the filled circle. Error bars denote standard error (n=3). Nystose data were generated by HPLC from assays performed under glucose inhibiting conditions. Sucrose consumption under normal and glucose inhibiting conditions was quantified by Fourier transform mid-infrared spectroscopy. Relative inhibition was expressed as the difference in sucrose consumption between the two conditions divided by uninhibited activity. Data were normalised to the parental activity. The most improved variants in terms of nystose production and/or relative inhibition are labelled.

Modifications to the *Aspergillus japonicus* β-fructofuranosidase enzyme which result in improved synthesis of inulin-type fructooligosaccharides (FOS) from sucrose are described herein.

Semi-rational directed evolution of the *A. japonicus* β-fructofuranosidase using a combination of strategies was performed and is described below. Only loop regions were selected for engineering using a crystal structure-guided approach, and amino acid substitutions were selected based on scoring positions in homologous protein sequence alignments using sequence entropies and solvent accessibilities. 36 variants of the β-fructofuranosidase, each with a single amino acid substitution, were engineered and this library was screened in *Saccharomyces cerevisiae* for variants that produced higher levels of FOS than the parent (wild type) enzyme. Enzymes were further screened for those producing more FOS than the parent under glucose inhibiting conditions. This strategic combination likely resulted in the enriched functionality of the library—58% of the first round library was active (these results are in contrast to the results of a similar strategy which focused on engineering loops, where site saturation mutagenesis at 90 loop residues in a lipase only yielded 10% of active mutants that were improved relative to the parent [65]).

Hits from the first round of screening were exhaustively combined to create a second library of combination variants with 2, 3 or 4 mutations, and a second round of screening was conducted to find combination variants with improved activity.

The amino acid substitutions mentioned below will be referred to relative to their position in the crystal structure of the mature polypeptide. The corresponding amino acid position in any of SEQ ID NOS: 3-21 can be calculated by subtracting 19 from the crystal position, and this position number is shown in parenthesis in some of the substitutions described below. In the claims, the position numbers of the amino acid residues into which substitutions are introduced correspond to the amino acid residues of the amino acid sequences represented by SEQ ID NOs: 3-21.

In the present invention, "substitution" means that a specific amino acid residue at a specific position is removed and another amino acid residue is inserted into the same position.

Modification to the *A. japonicus* β-fructofuranosidase polypeptide at positions 140, 178, 321 and/or 490 corresponding to the crystal structure of the mature polypeptide (corresponding to amino acids 121, 159, 302 and/or 471 of SEQ ID NOs: 3-21)) showed improved enzyme activity. Preferred modifications are substitution of the phenylalanine reside at position 140 (121) with a tyrosine residue, substitution of the alanine residue at position 178 (159) with a proline or serine residue, substitution of the glycine residue at position 321 (302) with an asparagine, aspartic acid, tyrosine or glutamic acid residue, and/or substitution of the glutamine residue at position 490 (471) with a serine, lysine or asparagine residue. More particularly, the substitution at position 140 (121) can be a tyrosine residue, the substitution at position 178 (159) can be a proline residue, the substitution at position 321 (302) can be an asparagine residue, and/or the substitution at position 490 (471) can be a serine residue. Consequently, a variant polypeptide of SEQ ID NO: 3 which has all four of the following amino acid residues does not fall within the scope of the present invention: phenylalanine at position 121, alanine at position 159, glycine at position 303 and glutamine at position 471. A178P and G321N were identified as positive contributors to thermostability. Proline substitutions in loops have been linked to improved thermostability due to backbone modifications that increase loop rigidity [58,66] and the data herein supports these findings.

71% of active mutants (15 variants) were improved over the parent. Data showed that the effect of combining the top 4 first round substitutions was cumulative and delivered the best variant instead of a 3 or 2 combination or even single substitution variant. One particular combination variant with 4 amino acid substitutions displayed a combination of improved thermostability and catalytic activity. This variant was designated "V1" and had the following modifications: F140Y-A178P-G321N-Q490S (F121Y-A159P-G302N-Q471S).

V1 had a specific activity that was 2-fold higher than that of the parent, and tested under conditions approximating its industrial application, V1 displayed an improved catalytic effectiveness than that of the parent by reducing the time to completion of the reaction by 22%. Extrapolation from the DSF thermostability data would suggest that V1 can be applied under reaction conditions at least 5° C. higher than currently employed, and it is probable that time to completion can be further reduced, as it is accepted that reactions kinetics are enhanced at elevated temperatures.

Previous improvements to fructosyltransferase activity of fungal β-fructofuranosidases have been achieved by altering amino acids in the active site pocket [23,24] and in the non-catalytic β-sandwich domain [21]. Although catalytic pocket residues seem the obvious choice for amino acid substitutions, the applicant has demonstrated that substitutions in solvent exposed loops mediate long range interactions which alter active site geometry and in turn modify enzyme activity.

In order to optimise expression of the modified polypeptide in a host cell, such as a microbial cell from a yeast (e.g. *Pichia pastoris*), fungus or bacterium, the polynucleotide encoding the modified polypeptide can be codon-optimised according to the host cell. Methods for codon-optimisation are well known to those skilled in the art. The polynucleotide can optionally include a secretion signal, such as that for *T. reesei* endoxylanase 2 (xln2) or any other suitable secretion signal. A vector including the polynucleotide can be used to transform the host cell. The polypeptide may be expressed under the control of various constitutive or inducible promoters, such as the *S. cerevisiae* phosphoglycerate kinase 1 (PGK1) promoter, glyceraldehyde-3-phosphate dehydrogenase (GAP) promoter or the alcohol oxidase (AOX1) promoter in *Pichia pastoris*. The transformed host cell can be added to a solution containing sucrose and be caused to express the polypeptide into the solution, possibly as whole cell catalysts, or alternatively a purified, partially purified or crude extract of the modified polypeptide can be added directly to the solution containing sucrose.

As described in more detail below, the β-fructofuranosidase gene (fopA) from *Aspergillus niger* ATCC 20611 (*A. japonicus*) was codon optimised for expression in *Pichia pastoris* DSMZ 70382 (purchased from the The Leibniz Institute DSMZ—German Collection of Microorganisms and Cell Cultures GmbH (Deutsche Sammlung von Mikroorganismen und Zellkulturen GmbH)). The protein was further engineered for higher specific activity, decreased glucose inhibition and thermostability by introducing the mutations of V1. The original enzyme (FopA) produced by the *P. pastoris* fopA strain was then compared to the protein-engineered enzyme (fopA_V1) produced by the *P. pastoris* G250.2 strain for its ability to produce a similar sugar composition from sucrose to Actilight®, a prebiotic ingredient which has been proven to have multiple health benefits and is extensively used in a wide variety of functional foods. Actilight®, available from Beghin Meiji and Teros Syral, contains scFOS in a ratio of 37%, 53% and 10% for GF2, GF3 and GF4, respectively.

The invention will now be described in more detail by way of the following non-limiting examples.

Example 1: Modification of β-Fructofuranosidase Variants

Materials and Methods
Microbial Strains and Media

*S. cerevisiae* EUROSCARFY02321 [BY4741; Mat a; his3Δ1; leu2Δ0; met15Δ0; ura3Δ0; YIL162w(SUC2)::kanMX4] served as host for the variant libraries [25]. The *S. cerevisiae* NI-C-D4 [Matα; trp1; ura3; pep4] oversecretion phenotype strain was used when heterologous proteins were to be purified [26]. *Escherichia coli* DH5α [fhuA2Δ(argF-lacZ)U169 phoA glnV44 φ80Δ (lacZ)M15 gyrA96 recA1 relA1 endA1 thi-1 hsdR17] (New England Biolabs, Midrand, South Africa) was used for cloning and amplification of plasmids. *E. coli* cells were grown at 37° C. in Luria Bertani broth supplemented with 100 µg/ml ampicillin or 50 µg/ml kanamycin, as appropriate.

DNA Manipulations

All DNA manipulations were performed according to standard methods [27]. Restriction enzymes and T4 DNA ligase were used according the specifications of the supplier (ThermoScientific, Waltham, Mass., USA). CLC Main Workbench version 6.8.1 (Qaigen) was used for sequence analyses.

Gene Synthesis and Mutagenesis

A codon-optimised (parent) gene was provided by DNA 2.0 (Menlo Park, Calif., USA) as a synthetic construct combining the *Trichoderma reesei* endoxylanase 2 (xln2) secretion signal [28] and the open reading frame of the fopA β-fructofuranosidase (GenBank accession number AB046383) (SEQ ID NO: 1 and 3). The native fopA secretion signal was excluded. Thirty-six variants of the β-fructofuranosidase gene were synthesised. The parent gene sequence was altered to produce gene products harbouring single amino acid substitutions. The substitutions were distributed throughout the protein sequence but were limited to loop regions as determined from the published crystal structure (3LF7) of Chuankhayan et al. [7]. The published crystal structures were determined for the *A. japonicus* β-fructofuranosidase. There is 99% homology on the DNA (AB046383, GU356596.1) and protein (BAB67771.1, ADK46938.1) levels of the β-fructofuranosidases of *A. niger* and *A. japonicus*, respectively. *Aspergillus niger* ATCC 20611 was reclassified by the curators of the ATCC culture collection (http://www.lgcpromochem-atcc.com) as *A. japonicus* and it was therefore assumed that the sequences and structures deposited in the databases are for the same gene/enzyme.

Positions for amino acid substitutions were selected by the strategy provided by DNA2.0. An alignment of homologous sequences to the 3LF7 structure was used from the HSSP database [29]. Positions within the MSA corresponding to secondary structural elements of the 3LF7 chain A were excluded. The solvent accessibility computed for each sequence position was normalised according to values obtained for Ala-X-Ala tripeptides [30,31]. This provided a relative solvent accessibility at each position normalized by the side chain type. The sequence entropy for each position in the multiple sequence alignment was also obtained from the HSSP file for RCSB Protein Data Bank entry 3LF7. Sequence positions with relative solvent accessibility (RSA) greater than 50% and sequence entropy (SE) greater than 1.0 provided a list of positions in the structure-based multiple sequence alignment. From these alignment data, the most commonly observed substitutions were selected for inclusion in a 36 variant first round library. The mutations are listed in Table 1. A further 18 genes were synthesised containing exhaustive combinations of 5 single mutations that were determined to improve enzyme performance during first round screening (Table 2). The amino acid sequences of these variants are shown in SEQ D NOS: 4-21.

TABLE 1

Single amino acid substitutions made to the parent enzyme to generate the first round library of β-fructofuranosidase variants.

| Amino acid substitution | Position on crystal structure (3LF7A) | Position in SEQ ID NOs: 3-21 | Module | Relative solvent accessibility (%) | Sequence Entropy | Enzyme activity* |
|---|---|---|---|---|---|---|
| P28A | 28 | 9 | β-propeller | 64 | 1.0 | Active |
| G109S | 109 | 90 | β-propeller | 79 | 1.5 | Inactive |
| F140Y | 140 | 121 | β-propeller | 50 | 2.0 | Active |
| F140S | 140 | 121 | β-propeller | 50 | 2.0 | Inactive |
| F140T | 140 | 121 | β-propeller | 50 | 2.0 | Inactive |
| F140R | 140 | 121 | β-propeller | 50 | 2.0 | Inactive |
| A178P | 178 | 159 | β-propeller | 55 | 1.7 | Active |
| A178S | 178 | 159 | β-propeller | 55 | 1.7 | Active |
| A178Y | 178 | 159 | β-propeller | 55 | 1.7 | Inactive |
| D185N | 185 | 166 | β-propeller | 65 | 1.2 | Inactive |
| D185H | 185 | 166 | β-propeller | 65 | 1.2 | Inactive |
| D185Q | 185 | 166 | β-propeller | 65 | 1.2 | Inactive |
| Y261S | 261 | 242 | β-propeller | 67 | 2.0 | Inactive |
| Y261N | 261 | 242 | β-propeller | 67 | 2.0 | Inactive |
| Y261T | 261 | 242 | β-propeller | 67 | 2.0 | Inactive |
| G321N | 321 | 302 | β-propeller | 56 | 2.1 | Active |
| G321D | 321 | 302 | β-propeller | 56 | 2.1 | Active |
| G321E | 321 | 302 | β-propeller | 56 | 2.1 | Active |
| G321Y | 321 | 302 | β-propeller | 56 | 2.1 | Active |
| E389N | 389 | 370 | β-propeller | 100 | 1.0 | Active |
| E389A | 389 | 370 | β-propeller | 100 | 1.0 | Inactive |
| E389K | 389 | 370 | β-propeller | 100 | 1.0 | Inactive |
| D454Q | 454 | 435 | β-propeller | 78 | 2.1 | Active |
| D454G | 454 | 435 | β-propeller | 78 | 2.1 | Active |
| D454T | 454 | 435 | β-propeller | 78 | 2.1 | Inactive |
| E485P | 485 | 466 | β-sandwich | 96 | 2.2 | Active |
| E485Q | 485 | 466 | β-sandwich | 96 | 2.2 | Active |
| E485N | 485 | 466 | β-sandwich | 96 | 2.2 | Active |
| E485S | 485 | 466 | β-sandwich | 96 | 2.2 | Active |
| Q490S | 490 | 471 | β-sandwich | 69 | 2.4 | Active |
| Q490K | 490 | 471 | β-sandwich | 69 | 2.4 | Active |
| Q490N | 490 | 471 | β-sandwich | 69 | 2.4 | Active |
| T569P | 569 | 550 | β-sandwich | 56 | 1.7 | Active |
| T569N | 569 | 550 | β-sandwich | 56 | 1.7 | Active |
| T569A | 569 | 550 | β-sandwich | 56 | 1.7 | Active |
| N648D | 648 | 629 | β-sandwich | 65 | 1.3 | Inactive |

Cloning and Yeast Library Generation

Cloning vectors (pJ227) containing the synthesised gene variants were digested with EcoRI and XhoI restriction enzymes (Fermentas) and directly ligated with the pJC1 yeast expression vector [32] digested with the same restriction enzymes. Selection of *E. coli* transformants on LB agar plates supplemented with 100 lg/ml ampicillin ensured isolation of clones with the gene variant—pJC1 combination and not re-circularised gene variant—pJ227, as the cloning vector conferred resistance to kanamycin. The primer pair 5'GTTTAGTAGAACCTCGTGAAACTTA 3' (SEQ ID NO: 22) and 5'ACTTAAAATACGCTGAACCCGAACAT3' (SEQ ID NO: 23) was used to screen clones by polymerase chain reaction to ensure the presence of the 2000 base pair insert. Positive clones were further confirmed by restriction digest analysis. Yeast was transformed by the lithium acetate method described by Hill et al. [33]. The method was adapted to 96-well format by proportionally scaling down reagents.

Yeast Cultivation and Media

*S. cerevisiae* was cultivated at 30° C. in YPD (1% yeast extract, 2% peptone and 2% glucose) or in synthetic medium, SC without uracil [2% carbon source, 0.67% yeast nitrogen base without amino acids (with ammonium sulphate; Difco Laboratories, Detroit, Mich., USA) and 0.13% amino acid dropout pool [34]]. Glucose and galactose served as carbon source in solid and liquid SC$^{-ura}$ media, respectively. Solid media contained 2% agar (Difco Laboratories).

Three yeast transformants per variant were manually transferred to individual wells of 2 ml round bottomed 96-deep-well plates (Merck, Modderfontein, South Africa) containing 1.25 ml SC$^{-ura}$ media. Mixing was facilitated by a single 2-mm glass bead (Merck, Modderfontein, South-Africa) added to each well. Plates were sealed with sterile, breathable AeraSeal™ film (Excel Scientific Inc., Victorville, Calif., USA) and shaken at 200 rpm for 4 days. Fifty microliters of each culture were transferred to a fresh plate and cultivated for a further 4 days. Master plates were generated using a 96-well replicator (Applikon Biotechnology, Delft, Netherlands). Culture supernatants were used in assays as source of enzyme after cell removal by centrifugation at 3000 rpm.

Library Screening

Enzyme activity assays were performed in 96-well format by reacting 50 µl of culture supernatant with 50 µl of substrate at 55° C. for 2 hours. The working concentration of substrate was 200 g/l sucrose (Fluka, Sigma-Aldrich, St. Louis, Mo., USA) in 50 mM citrate phosphate buffer, pH 5.5. As determined previously [22], 54 g/l glucose was added to the substrate solution to test for variants insensitive to product inhibition. Saccharides in assay samples were quantified using high performance liquid chromatography and Fourier transform mid-infrared (FT-MIR) spectroscopy. The details of the methods were described previously [22]. The rationale for supplying galactose as carbon source in liquid cultures was the separation of glucose and galactose by HPLC and hence any glucose present in assay samples was attributed to enzyme activity. Inhibition was calculated as the difference between uninhibited variant activity and inhibited activity divided by uninhibited activity. Data were normalised to the parental activity. The parent and all variants were was cultivated and assayed with triplicate repeats. The cultivation and assay procedure was validated previously [22].

Protein Purification

The top five performing variants were purified using immobilised metal affinity chromatography (IMAC). The proteins were N-terminal His-tagged by sub-cloning BglII-XhoI gene fragments into the same sites in a modified pJC1 yeast expression vector. The vector was modified by cloning a synthetic fragment (Geneart, Regensburg, Germany) encoding the xyn2 secretion signal, six histidine residues and a factor Xa protease cleavage site into the EcoRI and BglII sites of the multiple cloning site (ATG-GTTTCTTTCACATCCTTGTTGGCTGGTGTTGCTGCT-ATTTCCGGTGTTTG GCTGCTCCAGCTGCTGAAGT-

TABLE 2

Activity data for combination variants. Data are arranged in order of decreasing nystose per number of substitutions. Values in brackets are standard error (n = 3). The five most improved variants are coded.

| Number of substitutions | F140Y * | A178P * | A178S * | G321N * | Q490S * | Glucose (g/l) | Fructose (g/l) | Sucrose (g/l) | 1-Kestose (g/l) | Nystose (g/l) |
|---|---|---|---|---|---|---|---|---|---|---|
| 4 (V1) | x | x |  | x | x | 74.6 (±3.4) | 14.5 (±0.9) | 177.7 (±1.3) | 67.2 (±0.5) | 53.8 (±2.0) |
| 4 | x |  | x | x | x | 50.3 (±19.6) | 14.6 (±6.1) | 186.1 (±3.0) | 71.9 (±6.4) | 33.3 (±1.5) |
| 3 (V4) |  | x |  | x | x | 68.1 (±1.6) | 11.2 (±0.6) | 177.8 (±0.6) | 63.1 (±0.9) | 50.8 (±1.5) |
| 3 (V5) | x | x |  |  | x | 69.0 (±3.9) | 12.0 (±1.2) | 180.2 (±3.0) | 61.0 (±3.7) | 47.4 (±2.5) |
| 3 (V3) | x | x |  | x |  | 67.0 (±0.5) | 14.1 (±2.0) | 176.5 (±2.2) | 65.3 (±1.4) | 47.0 (±0.7) |
| 3 | x |  |  | x | x | 64.8 (±0.9) | 10.2 (±1.6) | 173.4 (±2.9) | 75.0 (±1.0) | 42.4 (±2.3) |
| 3 |  |  | x | x | x | 60.6 (±0.6) | 12.0 (±0.4) | 168.4 (±0.8) | 80.7 (±0.2) | 34.2 (±0.6) |
| 3 |  | x | x | x |  | 58.7 (±0.6) | 22.3 (±0.5) | 167.1 (±1.5) | 80.6 (±0.6) | 34.0 (±0.4) |
| 3 | x |  | x | x |  | 47.3 (±1.0) | 18.4 (±1.5) | 119.9 (±1.1) | 86.5 (±1.1) | 15.6 (±0.7) |
| 2 (V8) |  | x |  | x |  | 67.1 (±1.4) | 15.3 (±0.8) | 174.1 (±0.9) | 69.2 (±2.5) | 47.4 (±0.6) |
| 2 |  |  | x |  | x | 57.7 (±7.5) | 11.5 (±0.6) | 176.5 (±3.2) | 72.2 (±1.1) | 44.7 (±1.6) |
| 2 | x |  |  | x |  | 66.3 (±1.1) | 12.9 (±1.9) | 173.1 (±0.5) | 79.3 (±1.1) | 44.3 (±1.2) |
| 2 |  | x | x |  |  | 67.3 (±5.8) | 14.0 (±0.8) | 172.2 (±0.2) | 81.4 (±1.3) | 42.0 (±0.9) |
| 2 |  | x |  |  | x | 21.0 (±9.4) | 12.2 (±1.8) | 178.7 (±3.5) | 59.0 (±8.0) | 37.6 (±5.2) |
| 2 | x |  |  |  | x | 54.2 (±9.2) | 16.0 (±5.9) | 173.2 (±3.3) | 76.8 (±2.4) | 34.7 (±4.1) |
| 2 |  |  | x | x |  | 59.3 (±1.3) | 17.0 (±1.2) | 165.0 (±0.7) | 85.2 (±1.8) | 34.4 (±0.6) |
| 2 | x |  | x |  |  | 57.8 (±1.7) | 15.0 (±1.4) | 170.1 (±4.4) | 76.1 (±7.1) | 34.2 (±4.4) |
| 2 |  |  | x |  | x | 61.1 (±1.8) | 13.1 (±0.3) | 167.5 (±2.7) | 87.5 (±2.4) | 33.6 (±0.9) |
| 1 |  | x |  |  |  | 43.5 (±21.3) | 10.8 (±0.4) | 180.8 (±5.7) | 77.2 (±2.6) | 40.1 (±2.1) |
| 1 |  |  | x |  |  | 49.0 (±11.5) | 13.2 (±0.6) | 175.3 (±6.2) | 79.1 (±1.8) | 37.6 (±1.4) |
| 1 |  |  |  |  | x | 48.5 (±13.0) | 16.3 (±3.1) | 174.9 (±3.0) | 83.7 (±3.0) | 33.8 (±3.0) |
| 1 | x |  |  |  |  | 59.2 (±1.0) | 15.3 (±1.2) | 165.1 (±2.9) | 82.9 (±1.3) | 32.9 (±1.9) |
| 1 |  |  |  | x |  | 46.7 (±6.4) | 18.7 (±4.0) | 164.2 (±4.7) | 68.0 (±19.7) | 22.8 (±2.3) |
| Parent | — | — | — | — | — | 44.1 (±14.9) | 17.7 (±3.7) | 166.1 (±2.2) | 69.1 (±12.8) | 32.6 (±1.2) |

* Substract 19 to calculate amino acid position in SEQ ID NOs: 3-21

TGAATCCGTTGCTGTTGAGAAGagaCATCACCATCA CCATCAC GGATCcGGCTCTGGATCTGGTATC- GAGGGAAGA (SEQ ID NO: 24). Tagged gene variants were sequenced to verify integrity of the clones. Plasmids were transformed to *S. cerevisiae* NI-C-D4. Transformants were cultivated for 72 hours in 50 ml double strength SC$^{-ura}$ buffered with succinic acid at pH 6.0 [(2% glucose, 1.34% yeast nitrogen base without amino acids (with ammonium sulphate; Difco Laboratories, Detroit, Mich., USA) and 0.26% amino acid dropout pool [34]]. Antifoam 204 (Sigma-Aldrich, St. Louis, Mo., USA) was added after 48 hours of cultivation to a concentration of 0.025% (v/v). Following cell removal by centrifugation, supernatants were concentrated 50 times by ultrafiltration using Amicon ultra-15 centrifugal filters with 10 kDA MWCO (Millipore, Molsheim, France). IMAC protein purification was performed under native conditions using Ni-NTA spin columns supplied by Qaigen (Venlo, Netherlands). For the removal of imidazole, buffer exchange with 10 mM Bis-Tris, pH 6 was performed using the aforementioned ultrafiltration devices. Protein concentration was determined using the bicinchoninic acid assay (Pierce Chemical Company, Rockford, Ill., USA) with bovine serum albumin as standard.

Enzyme Assays

A unit of enzyme was defined as the amount of protein that produced 1 mmol 1-kestose per minute from 10% (w/v) sucrose at 40° C. in 50 mM citrate phosphate buffer (pH 5.5). The definition approximates that of Hirayama et al. [35].

Protein Electrophoresis

Samples were analysed by SDS-PAGE on an 8% resolving gel. Loading dye consisted of 60 mM Tris-HCl (pH 6.8), 25% glycerol, 2% SDS, 14 mM β-mercaptoethanol and bromophenol blue and gels were run in Tris-glycine buffer (25 mM Tris-HCl, 250 mM glycine, 0.1% SDS). Protein bands were visualized with a silver-stain [36].

Isothermal Denaturation (ITD) and Differential Scanning Fluorimetry (DSF)

Protein thermal denaturation assays were performed by the method described by Niesen et al. [37]. SYPRO orange was supplied by Sigma-Aldrich (St. Louis, Mo., USA) and used at a 5× working concentration. Each reaction utilised 65 ng of protein. Samples were incubated in a StepOnePlus Real-Time PCR machine (Applied Biosystems). IDT samples were incubated at 55° C. for 10 hours while DSF samples were incubated with temperature increasing by 1° C. per minute from 25-95° C. Multicomponent data were exported from the StepOne software to Excel 2010 and ROX filter data were used. Data points beyond the maximum fluorescence +4 were discarded. First derivatives were calculated in Statistica version 12 (StatSoft Inc.). In cases where 2 peaks were obtained after application of the derivative, the temperature of the second peak was used. One-way analysis of variance (ANOVA) was conducted to test for differences between treatments applied to enzymes.

Computational Analyses

Homology models for the single amino acid variants at the 4 positions yielding the most improved variants and the 5 best combination variants were generated by the SWISS-MODEL web server [38]. The crystal structure 3LF7 [7] served as template for the automated modelling mode. Template and target sequences shared 99% identity. Quality assessment of the models was performed by the QMEAN server (47).

Solvent accessible surface area (SASA) data for the most improved combination variant were generated from the homology model. SASAs were computed for the folded (from the homology models) and unfolded states (sequence specific theoretical calculations) by the ProtSA web server (51). Differences between the folded and mean unfolded ensembles were determined. To examine the influence of the amino acid substitutions on SASAs, differences between the parent and the variant were further calculated.

The Ligand-Protein Contacts (LPC) server was used to identify amino acid residues in contact with the ligand (first shell residues). Contacts with substituted residues in the variant were identified by the Contacts of Structural Units (CSU) server. Servers were accessed via http://ligin.weizmann.acil/cgi-bin/lpccsu/LpcCsu.cgi (67). Functional site predictions where made using 3LF7 structure as input for the Partial Order Optimal Likelihood (POOL) server (67). The top 8% of ranked residues were taken as active site residues.

FOS Synthesis

FOS synthesis was performed with the parent enzyme and the variant displaying the highest specific activity. It was accomplished by reacting 10 U of parent enzyme per gram of sucrose and dosing the same amount of protein for the variant. The reaction was performed at 62° C. with shaking at 120 rpm. Working concentrations were 600 g/l sucrose dissolved in 50 mM citrate phosphate buffer, pH 5.5. Samples were taken hourly for 12 hours and analysed by HPLC after appropriate dilution.

Results

Round 1: Single-Amino-Acid Substitution Library Screening

Table 1 and FIG. 1 list the amino acid substitutions selected to generate the first round of variants. Although the substitutions were limited to the loop regions, they were otherwise distributed across the entire protein sequence length. Substitutions were made at 13 positions with multiple substitutions at 10 of the positions. Of the 36 variants, two were deemed inactive as evidenced by a lack of growth on solid media supplemented with sucrose as sole carbon source. Active gene products complemented the suc2 knockout in the *S. cerevisiae* strain enabling growth on sucrose containing solid media. The activities of a further 10 variants were deemed severely compromised as HPLC and FT-MIR spectroscopy indicated negligible amounts of sucrose conversion. SDS-PAGE analyses showed consistent protein expression levels for the variants, barring three where protein production was abolished—expected bands were absent. The activities of these three variants remained unknown (data not shown). The sensitivity of the catalytic β propeller domain of FopA to structural alterations was highlighted by 48% of substitutions resulting in abolished or severely compromised activities as opposed to the β sandwich domain where all variants remained active bar one (9%), the activity of which remains unknown. FIG. 2 shows the nystose and relative inhibition data for the 21 variants retaining good activity levels. The smaller the relative inhibition value the less sensitive the enzyme to glucose inhibition. Variant A178S appeared to tolerate glucose better than other variants but at the expense of its fructosyltransferase activity. First round screening data were used to design combination variants of the top five performing round 1 variants. The top four nystose producing variants F140Y, A178P, Q490S and G321N and the single variant showing the greatest relief from glucose inhibition (A178S) were combined exhaustively to produce another 18 variants which included combinations of two, three and four amino acid substitutions.

Round 2: Combination Variant Screening

Table 2 lists the combination variants grouped by number of substitutions and their activity data arranged per group in descending order for nystose. The parent (wild type) data is given in bold font. Sixteen of the 18 variants showed improved activity relative to the parent. Besides the single substitution variant A178S, only F140Y-A178S-G321N displayed poorer fructosyltransferase activity than the parent. Furthermore, all the variants with the A178S substitution performed worse than the variants with the A178P substitution. Although combining A178S with other substitutions did recover activity relative to the parent, it was generally assumed to be a deleterious substitution and did not prove permissive in a combinatorial context. No trend emerged for relative inhibition of combination variants and the A178S substitution (data not shown). Single substitutions ranked in decreasing order of nystose production A178P, G321N, Q490S, F140Y and A178S. A178P and G321N always proved to be good substitutions be it in isolation, in combination with each other and with either Q490S and/or F140Y. The contributions of Q490S and F140Y to enzyme activity were combination dependent. Together in a combination of 2 they were the poorest performers of the combination mutants. When combined with A178P, F140Y improved enzyme activity to a greater degree than Q490S—37.6 g/l nystose produced as opposed to 34.7 g/l. In a combination of 2 with G321N, both F140Y and Q490S resulted in the same amount of nystose produced at approximately 44 g/l. However, the 1-kestose values differed with F140Y-G321N levels at 79.3 g/l while G321N-Q490S levels were 72.2 g/l. It is probable that G321N-Q490S was a more efficient enzyme as decreasing 1-kestose levels with similar nystose levels indicate GF4 production. No significant differences in the levels of sucrose, glucose and fructose supported this deduction. For a 3 combination variant the opposite for Q490S was true—A178P-G321N-Q490S produced more nystose than F140Y-A178P-G321N. The 4 combination variant F140Y-A178P-G321N-Q490S proved to be the most improved variant with nystose levels 65% higher than the parent—53.8 g/l versus 32.6 g/l.

Improved Variant Characterisation

This section applies to the parent and the five most improved combination variants. For simplicity the combination variants were named V1: F140Y-A178P-G321N-Q490S (F121Y-A159P-G321N-Q471S), V3: F140Y-A178P-G321N (F121Y-A159P-G302N), V4: A178P-G321N-Q490S (A159P-G302N-Q471S), V5: F140Y-A178P-Q490S (F121Y-A159P-Q471S) and V8: A178P-G321N (A159P-G302N).

Protein Purification and Electrophoresis

Figure 3:
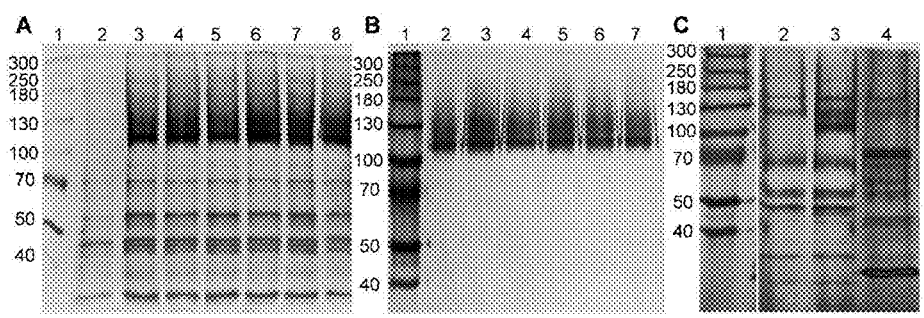
FIG. 3: SDS-PAGE gels of purified (A) and crude (B, C) parent and five most improved combination variant β-fructofuranosidases. All gels were 8% and silver stained. B shows crude supernatants of $S.$ $cerevisiae$ NI-C-D4[fopA]. Lane 2 is a reference as yeast was transformed with empty vector pJC1. Lanes 3 to 8 show the parent and the five most improved variants. A shows the IMAC purified enzymes. Lanes 2 to 7 show the parent and variant enzymes. C shows the result of PNGase treatment of the crude supernatant (parent). Lane 2 control, lane 3 untreated and lane 4 treated sample. The Spectra multicolor high range protein ladder (Thermo Scientific) was loaded in lane 1 of all the gels and served as molecular weight marker.

Enzymes were purified using IMAC. FIG. 3 shows the purified enzymes and crude yeast supernatants on a silver stained SDS-PAGE gel. The high degree of enzyme purity following IMAC is evident in gel A. The intense bands between 100 and 130 kDa correspond to the parent and variant β-fructofuranosidases—the band was absent in the reference (gel B, lane 2). The proteins were larger than the expected 69 kDa as deduced from the protein sequence but the shift was attributed to N-glycosylation of the proteins by yeast. Following the removal of the glycosylation with PNGase F, bands of the expected size were obtained (gel C, lane 4). All variants had 8 putative N-glycosylation sites which was unchanged from the glycosylation pattern of the parent [40]. Chuankhayan et al. [7] proposed that altered N-glycosylation patterns from heterologous hosts may influence enzyme stability. As the parent and all variants were expressed in the same host this was irrelevant but altered stability was ruled out due to altered N-glycosylation patterns resulting from different primary protein structures of the variants.

Specific Activity

Figure 4:
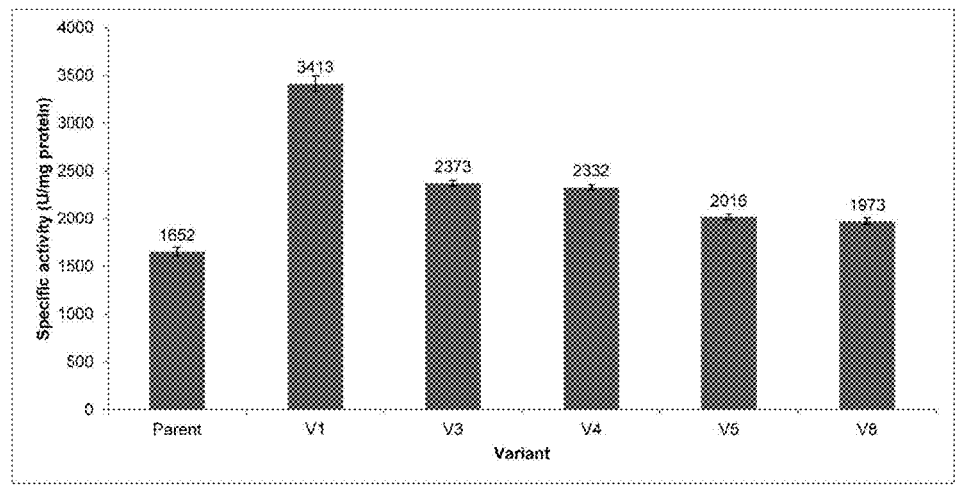
FIG. 4: Specific activity data for the purified parent and five most improved combination variants. Values above each bar indicate the average 1-kestose units per milligram purified enzyme. Error bars denote standard error (n=3).

Specific activities for the purified enzymes were determined. Results are shown in FIG. 4. The specific activity of the parent enzyme was 1652 U/mg protein which was lower than the 2650 U/mg protein reported by Nishizawa et al. [19]. Heterologous enzyme production and experimental disparities could account for this. Differences in activity between the native enzyme and the heterologous fopA gene product were also reported by Yanai et al. [41]. All the variants had significantly (p=0.0023 for V8) higher specific activities than the parent, with V1 as much as double.

Isothermal Denaturation (ITD)

Figure 5:
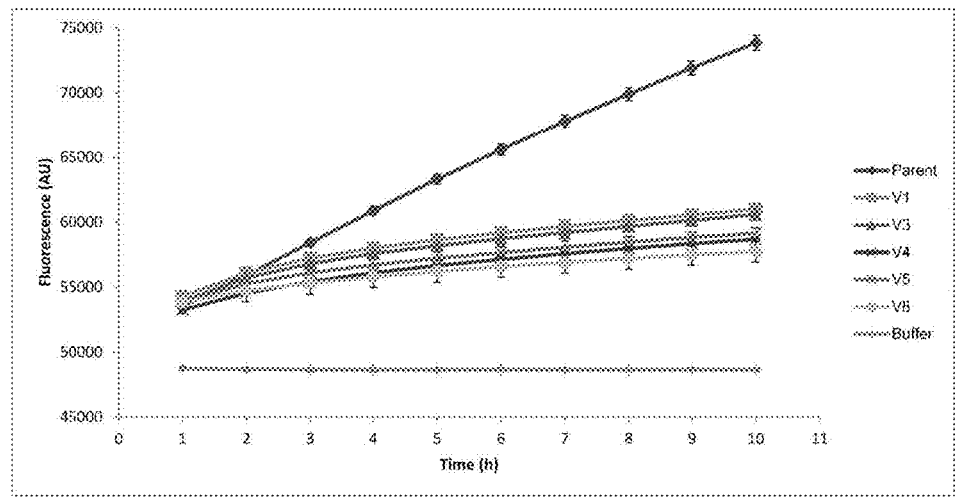
FIG. 5: Isothermal denaturation data for the parent and five most improved combination variants. Purified proteins were incubated with SYPRO orange at 55° C. and fluorescence was monitored for 10 hours. Increased fluorescence indicates thermal denaturation of the protein as SYPRO orange binds to newly exposed hydrophobic amino acids. Error bars denote standard error (n=5).

To investigate the stability of the improved variants, ITD (a method that quantifies protein stability by measuring protein unfolding caused by heat denaturation in the presence of SYPRO orange dye [42]) was employed. Typically this method is used to quantify stability and ligand affinity for a given protein. The method was employed in a modified sense in that the proteins were the variable factor. Purified proteins were incubated for 10 hours at 55° C. to examine the influence of protracted exposure to temperatures routinely used for industrial FOS synthesis reactions. FIG. 5 shows that after 2 hours the fluorescence measured for the parent enzyme increased dramatically whereas the variants showed more measured increases. The increased fluorescence can be interpreted as thermal denaturation of the enzymes. Upon protein unfolding, binding of the SYPRO orange dye to newly exposed hydrophobic amino acid residues results in increased fluorescence [43]. It thus appeared that the variant enzymes were more thermostable than the parent. Slight differences in stability were observed between the variants, which could be attributed to the differing combinations of amino acid substitutions.

Differential Scanning Fluorimetry (DSF)

Melting Temperatures ($T_m$) and pH Optima

To further investigate the thermostability of the variants, DSF [37] was employed. The principle is similar to ITD, but instead of maintaining a set temperature, it is increased by 1° C. per minute. The $T_m$ of a protein is the temperature at which half of the protein molecules are unfolded and reflects the transition midpoint of the fluorescence vs temperature curve [37,44,45]. Factors influencing protein stability include buffers, salts and detergents and also specific interactions with ligands. Factors that promote stability delay the thermally induced unfolding and result in increased $T_m$. DSF experiments were conducted for the parent and 5 variants at pHs ranging from 4 to 7. Fluorescence intensity curves for the parent displayed the typical two-state unfolding transition (folded to unfolded with no stable intermediates) [37, 46] at all pH levels tested. However, all the variant profiles were pH dependent. At low pH the unfolding proceeded via the typical two-state transition while at higher pH unfolding occurred in via multiple-state transitions. This was attributed to a mutation(s) that stabilised a portion of the protein and thus more energy was required for complete unfolding. The maximum fluorescence at pH 4 was in excess of 60000 AU, whereas at pH 7 it was 22000 AU. Hirayama et al. [35] reported the optimum pH for the wild type enzyme in terms of activity and stability to be between 5 and 6 and 6.5, respectively. At pHs below 4.5 the stability and activity of the enzyme were severely compromised. The high fluorescence and two-state transition of the variant proteins at low pH were therefore attributed to the severely unfavourable conditions imposed on the enzyme at pH 4. The ionization states of amino acids were likely altered and hence contributed to extensive protein denaturation. $T_m$s were calculated from the first derivatives applied to the fluorescence data

Figure 6:
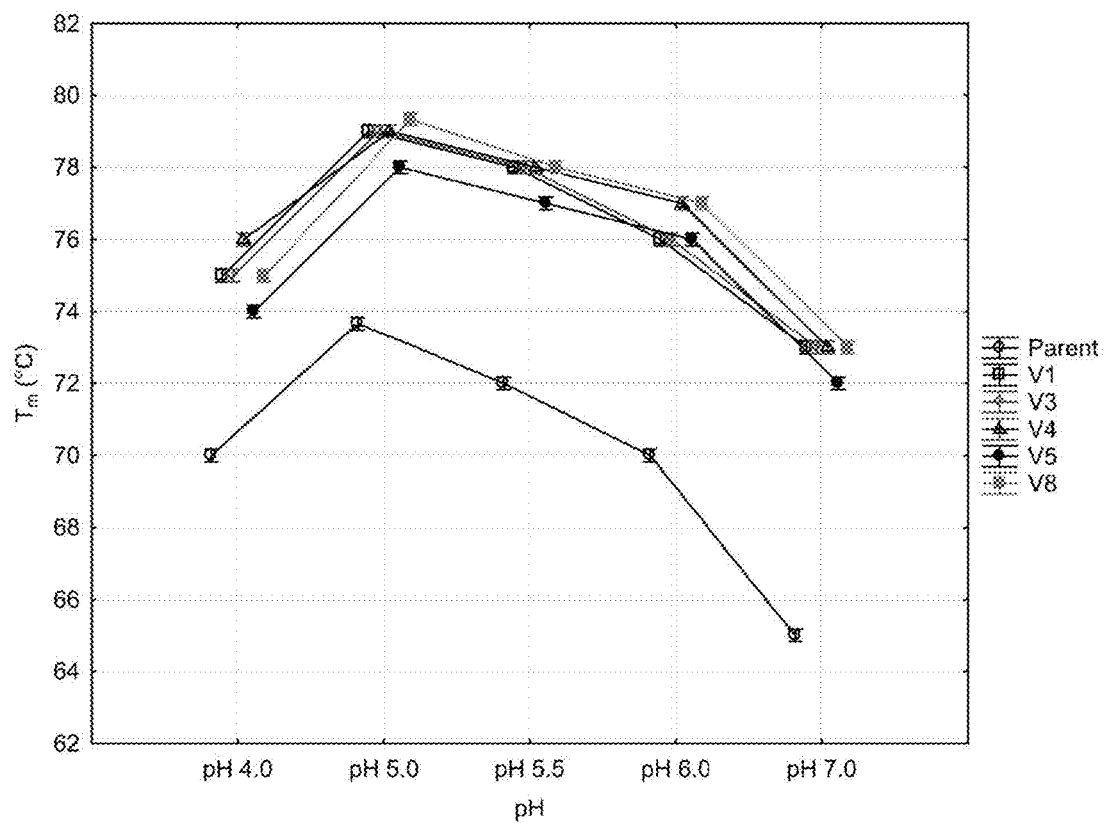
FIG. 6: Differential scanning fluorimetry-derived melting temperatures for purified parent and five most improved combination β-fructofuranosidase variants at pHs ranging from 4-7. Error bars denote 0.95 confidence intervals (n=3).

[37]. For samples presenting multiple transitions the maximum of the second peak was used to determine the $T_m$. The results at each pH for the enzymes are shown in FIG. 6. Similar to the ITD results, it was clear that the variants were more thermostable than the parent. The pH optima profiles did not change due to amino acid substitution—the optima for all enzymes were at pH 5.0. At optimum pH V8 displayed a 5.7° C. increased $T_m$ relative to the parent (73.7° C.), making it the most thermostable variant. V1, V3 and V4 all displayed improvements of 5.3° C., while V5 was improved by 4.3° C. The differences between the three $T_m$ groups were all statistically significant (p<0.05). Considering the combinations of substitutions in the variants, A178P and G321N appeared to be responsible for the improved thermostability. All variants harboured the A178P substitution and they were all more stable than the parent. As V1 (F140Y-A178P-G321N-Q490S), V3 (F140Y-A178P-G321N) and V4 (A178P-G321N-Q490S) all displayed the same improvement, it appeared that F140Y and Q490S were marginally destabilising substitutions in terms of thermostability—inclusion of either one or both of them resulted in a decreased $T_m$ relative to V8. As V8 (A178P-G321N) was the most improved and V5 (F140Y-A178P-Q490S) the least which was concluded was that G321N contributed positively to stability.

Ligand Affinities

Figure 7:
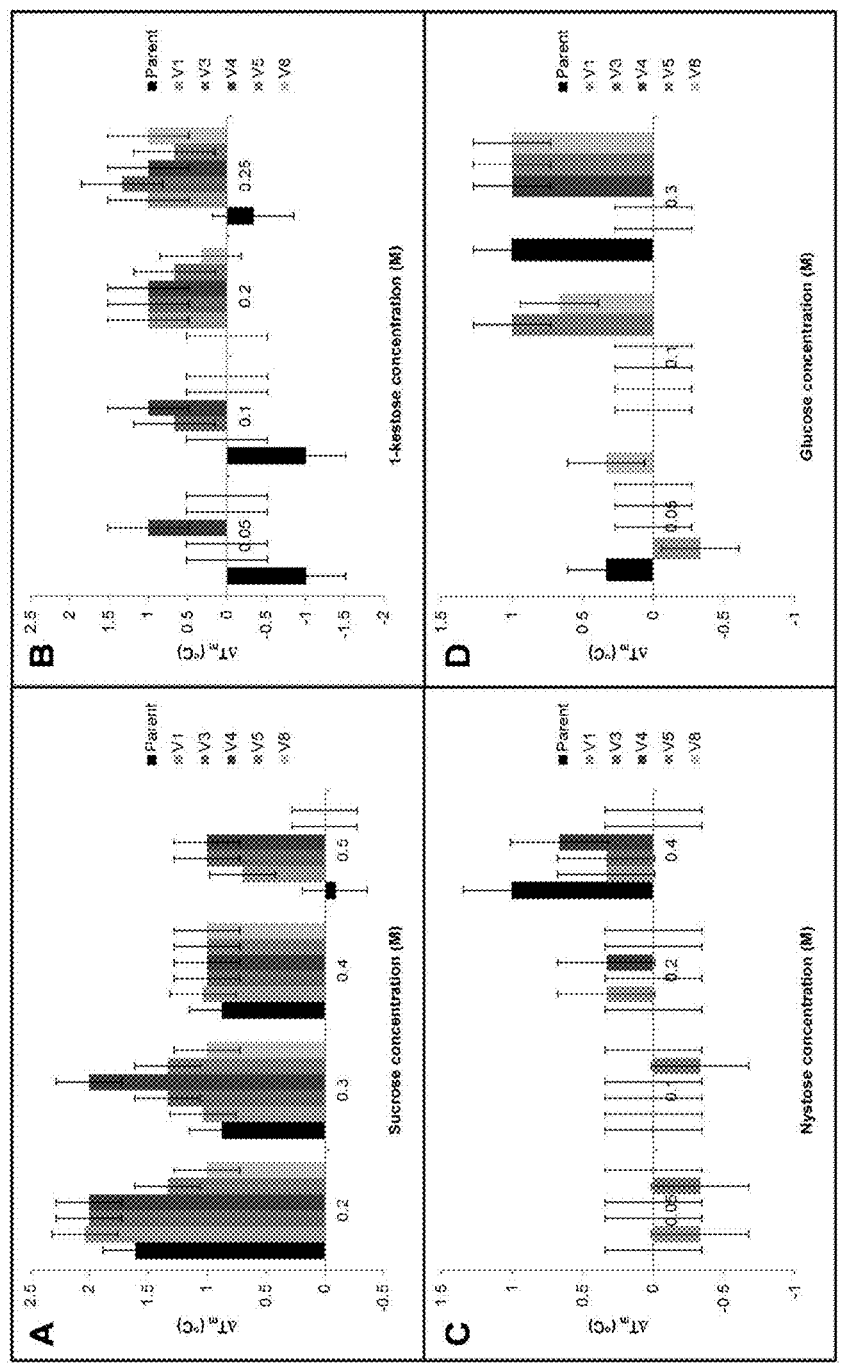
FIG. 7: $\Delta T_m$ values for the parent and 5 most improved combination variants in the presence of substrates sucrose (A), 1-kestose (B) and nystose (C). Differences between the given concentrations and the zero substrate $T_m$s are shown. Error bars denote 0.95 confidence intervals (n=3).

Although V8 was the most thermostable enzyme, it did not display the highest specific activity. DSF was used to perform comparative investigations into substrate interactions between the parent and variant proteins. More effective ligand binding to enzymes results in delayed thermal denaturation and higher $T_m$s. Results for $\Delta T_m$ ($T_m$ at given substrate concentration minus $T_m$ at 0 substrate concentration) at different substrate and product concentrations are shown in FIG. 7. At 0.2 M sucrose increased $T_m$s were observed for all enzymes (FIG. 7A). Further increased sucrose concentrations resulted in diminished substrate binding for all enzymes as evidenced by lower $T_m$s. At 0.5 M sucrose the parent, V5 and V8 displayed the same $T_m$ as in the absence of substrate, whereas variants V1, V3 and V4 displayed increased $T_m$s—differences were small, $\otimes T_m$ of 1° C. or less, but significant (p<0.05 for V1, V3 and V4). It was apparent that the substrate binding at 0.5 M sucrose was altered for enzymes with higher specific activities, namely V1, V3 and V4 (FIG. 4). In the case of 1-kestose, all variants bound the substrate with higher affinity than the parent (FIG. 7B). Increased 1-kestose concentrations increased the stability of all variants except V4 which did not display an altered $T_m$ at all concentrations tested. Enzyme stabilisation as a result of nystose binding was not evident at concentrations up to 0.2 M—no significant changes in $T_m$ were observed (FIG. 7C). However, at 0.4 M the parent and V4 were stabilised significantly by nystose binding. The other variants did not show significant improvements in $T_m$ as a result of substrate binding. Finally, binding of glucose (product) to enzymes was also examined and results indicated that the two most improved variants, V1 and V3, appeared to have diminished affinities for glucose—$T_m$s were not affected at glucose concentrations up to 0.3 M while the parent, V3, V4 and V5 were stabilised by 1° C. In summary, the most improved variant, V1, displayed increased affinities for sucrose and 1-kestose and decreased affinities for nystose and glucose at the highest substrate concentrations tested. The $T_m$ of the parent was unaffected by sucrose or 1-kestose while it was increased by nystose and glucose, again at the highest concentrations tested. Taken in combination, these data indicated that subtle changes to the range of substrate and product affinities as well as improved thermostability were responsible for improved enzyme activities. It is plausible that the amino acid substitutions altered the active site such that the enzymes were relieved to an extent from substrate and product inhibition, conditions that are well documented in the literature for β-fructofuranosidases, albeit not this specific enzyme. Further kinetic characterisation is required to fully understand the impact of substitutions on the enzymes' activities.

FOS Synthesis

Figure 8:
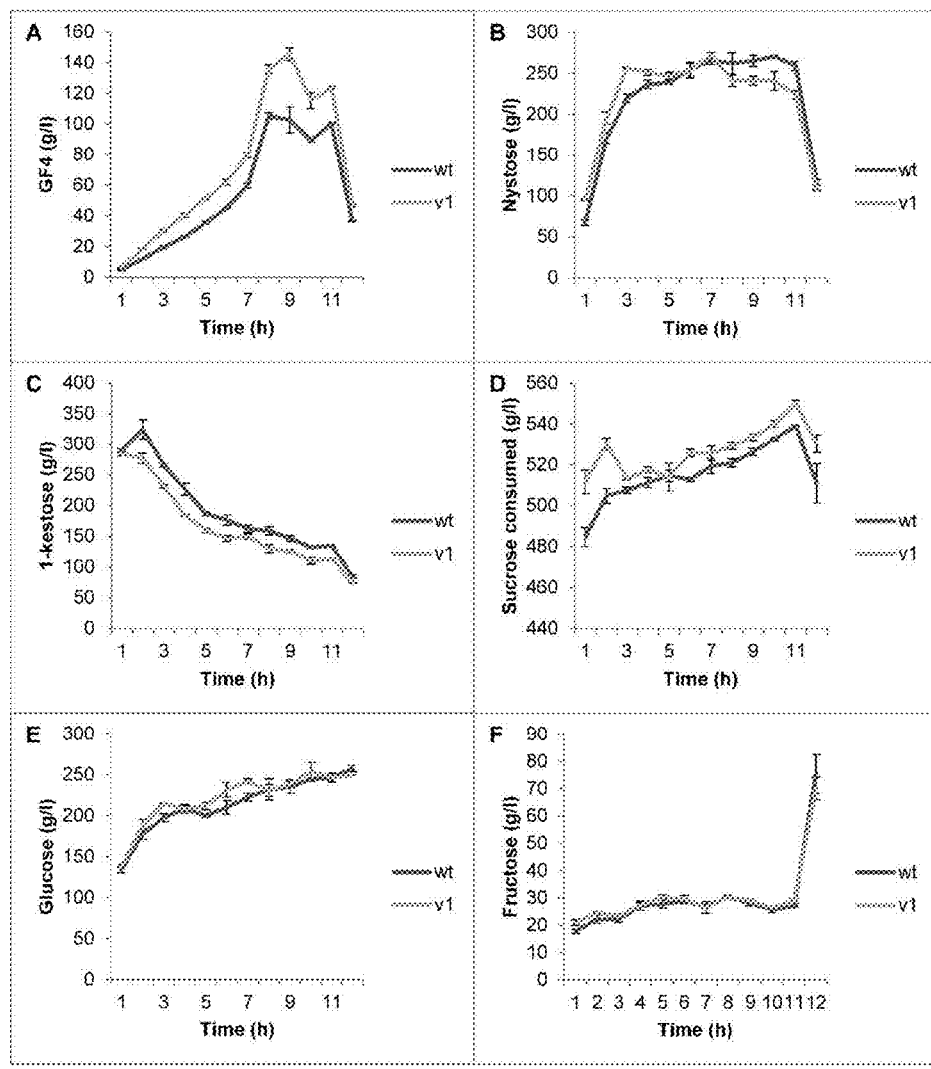
FIG. 8: Time course FOS synthesis by the purified parent and most improved variant (V1) enzymes. The enzyme dosage was 10 KU per gram sucrose with a starting concentration of 600 g/l sucrose. The reaction was conducted at 62° C., pH 5.5 with shaking at 120 rpm. Error bars denote standard error (n=3).

As an ultimate test of variant performance, equal amounts of purified parent enzyme and V1 were used to produce FOS under conditions similar to those used in industry. In commercial FOS products the ratio of GF2:GF3:GF4 is approximately 42:47:10 and depending on the product, compromise up to 95% of the dry mass after chromatographic separation of glucose, fructose and sucrose [19,60-62]. FIG. 8 shows HPLC data for all the relevant sugars. It was evident that V1 has a higher catalytic activity relative to the parent, as the levels of nystose and GF4 were higher. Higher 1-kestose levels for the parent highlighted the difference in activities as this is the initial FOS species produced from sucrose. It in turn serves as substrate for the formation of nystose and GF4. As equal amounts of protein were dosed, it can be deduced that V1 has a higher turnover number ($k_{cat}$) than the parent. The fructose data for both enzymes were virtually identical, which indicated that the hydrolytic activity was unchanged in the variant. V1 consumed marginally more sucrose than the parent, but it was not reflected in the amount of total FOS produced. As the differences in molecular weights between sucrose and FOS are large, experimental error could account for the discrepancy (a given amount of sucrose translates into a small amount of FOS which could be missed given a maximum of 10% error of quantification). Similarly for glucose, which is an indicator of global enzyme activity, clear differences at all the time points were not evident. Although the reaction was followed for 12 hours, the endpoint for a typical industrial reaction was regarded as the time when total FOS composition comprised 10% GF4. V1 reached 10% GF4 in 4.6 h while it took the parent 6.2 h to produce FOS of similar composition. This difference represented a 26% reduction in time required to complete the reaction. Otherwise stated, enzyme dosage could be reduced to achieve the same result in 6.2 h.

The hydrolytic activity of the enzyme dominated after 11 h as reflected by the sharp increase in fructose and corresponding decreases in GF4, nystose, sucrose and to a lesser extent, 1-kestose levels.

Example 2: Expression of V1 in *Pichia pastoris* and Conversion of Sucrose to FOS Materials and Methods Bioreactor Cultivations

*P. pastoris* cultivations were performed in 1.3 L New Brunswick Bioflo 110 Fermenters/Bioreactors with a working volume of 1 L. Biocommand version 3.30 plus software was used for monitoring and feed rate control. Pre-cultures were prepared by inoculating a streak of colonies from YPD agar plates into 4 ml of buffered minimal glycerol medium (BMGH) as described in the *Pichia* Expression Kit (Invitrogen) with the exception of a final YNB concentration of 0.17%. Following overnight incubation at 30° C. cultures were diluted to an optical density $(OD)_{600}$=0.1 in 40 ml of fresh BMGH medium. Subsequently, these seed-cultures were grown overnight at 200 rpm to an $OD_{600}$=10-15, before inoculating the entire volume to the medium to a final volume of 400 ml in the bioreactor, obtaining a starting $OD_{600}$=1.0-1.5.

Fermentation basalt salt medium (BSM), supplemented with 4% glycerol and $PTM_1$ trace salts, was used as culture media as described by the *Pichia* Fermentation protocol (Invitrogen). Culture conditions were maintained as follows: temperature of 30° C. and a pH of 5.0 was maintained with 28% ammonium hydroxide, aeration rate of 1.0 volume of oxygen per volume of fermentation culture per minute (vvm), the dissolved oxygen (DO) was maintained at 30% controlled by a cascade effect between agitation (200-1000 rpm) and sparging $O_2$ when agitation was not sufficient. Fermentations were performed as per the *Pichia* Fermentation protocol (Invitrogen) with the following exceptions: During the glycerol fed-batch phase the glycerol was fed via a DO-stat feeding strategy (feeding started when DO>=30% and stopped when it was <30%). This was continued for 72 hrs after the batch phase at which point the bioreactor volume was harvested, centrifuged for 3 min at 3000 rpm and then filtered through 22 μm filter and stored at 4° C. for determining the enzyme activity.

Enzyme Activity Assay

To determine the fructofuranosidase activity, sucrose was used as the substrate and prepared in a 50 mM citrate phosphate buffer (pH 5.5) and used at a working concentration of 100 g·l$^{-1}$. The substrate solution was equilibrated at 40° C. for 10 min where after culture supernatant was added to a final of 25% [v/v] and incubated for 60 min. To stop the reaction, perchloric acid (PCA) was added to a final concentration of 2.14% followed by the addition of 7 N KOH to precipitate the proteins prior to chemical analysis. Negative control reactions containing all the assay constituents except for either sucrose or enzyme were included. The samples were diluted appropriately and subjected to HPLC analysis using an external glucose standard calibration. The method has been described previously [69]. The concentration of glucose liberated during the assays was indicative of global fructofuranosidase activity. A unit of enzyme was defined as the amount of enzyme required to produce 1 μmol glucose per minute under the described conditions [14].

Fructooligosaccharide (FOS) Production

To produce scFOS, a 60% sucrose solution (w/v) was prepared in a 50 mM citrate phosphate buffer (pH 5.0). The substrate solution was equilibrated at the required temperature in a Gyrotory Water Bath Shaker (New Brunswick Scientific Co. Inc., Edison N.J., USA) for 2 min while shaking at 120 rpm where after culture supernatant was added at a predetermined dosage according to central composite design. Samples were taken every 2 hrs and the reaction stopped by adding perchloric acid (PCA) to a final concentration of 2.14% followed by the addition of 7 N KOH to precipitate the proteins prior to chemical analysis in a Dionex UltiMate 3000 (Thermo Fisher Scientific, Waltham Mass., USA).

Central Composite Design

The production of scFOS was optimised as a function of temperature and enzyme dosage using response surface methodology (RSM) with a two-factor central composite design using Design Expert® software (Stat-Ease Inc., Minneapolis, USA). The input factors in the design were selected in the ranges of 57° C.≤A≤67° C. and 8 U/g sucrose≤B≤12 U/g sucrose, where A represents the temperature and B the enzyme dosage. This design gave a total of 11 experiments for each enzyme (Tables 3 and 4).

TABLE 3

Central composite design of temperature (A) and enzyme dosage (B) for scFOS production by the enzyme fopA_V1 using 60% (w/v) sucrose solution for 8 hrs. Only time points where ~10% GF4 was produced are shown or where conditions did not achieve this the values for the final two time points are shown.

| Run no. | Factors A (° C.) | B (U/g sucrose) | Time (hrs) | % of total scFOS GF2 | GF3 | GF4 |
|---|---|---|---|---|---|---|
| 1 | 62.00 | 12.83 | 4 | 44.05 | 47.50 | 8.44 |
|  |  |  | 6 | 35.34 | 51.16 | 13.50 |
| 2 | 62.00 | 10.00 | 6 | 41.88 | 48.93 | 9.19 |
|  |  |  | 8 | 36.63 | 50.97 | 12.40 |
| 3 | 67.00 | 8.00 | 6 | 47.45 | 45.40 | 7.15 |
|  |  |  | 8 | 42.00 | 48.60 | 9.40 |
| 4 | 57.00 | 8.00 | 6 | 50.20 | 45.01 | 4.79 |
|  |  |  | 8 | 43.07 | 51.52 | 5.42 |
| 5 | 54.93 | 10.00 | 6 | 58.33 | 35.23 | 6.44 |
|  |  |  | 8 | 52.17 | 38.10 | 9.73 |
| 6 | 62.00 | 10.00 | 6 | 40.74 | 49.51 | 9.74 |
|  |  |  | 8 | 34.30 | 53.70 | 12.00 |
| 7 | 69.07 | 10.00 | 6 | 41.83 | 50.56 | 7.60 |
|  |  |  | 8 | 38.34 | 51.60 | 10.06 |
| 8 | 62.00 | 7.17 | 6 | 49.26 | 44.64 | 6.10 |
|  |  |  | 8 | 42.72 | 48.79 | 8.50 |
| 9 | 57.00 | 12.00 | 6 | 40.29 | 51.69 | 8.03 |
|  |  |  | 8 | 34.05 | 54.49 | 11.46 |
| 10 | 67.00 | 12.00 | 4 | 44.90 | 47.46 | 7.64 |
|  |  |  | 6 | 36.94 | 51.02 | 12.03 |
| 11 | 62.00 | 10.00 | 6 | 41.51 | 48.00 | 10.50 |
|  |  |  | 8 | 35.18 | 50.44 | 14.38 |

TABLE 4

Central composite design of temperature (A) and enzyme dosage (B) for scFOS production by the enzyme fopA using 60% (w/v) sucrose solution for 8 hrs. Only time points where ~10% GF4 was produced are shown or where conditions did not achieve this the values for the final two time points are shown.

| Run no. | Factors A (° C.) | B (U/g sucrose) | Time (hrs) | % of total scFOS GF2 | GF3 | GF4 |
|---|---|---|---|---|---|---|
| 1 | 62.00 | 12.83 | 6 | 40.43 | 49.60 | 9.97 |
|  |  |  | 8 | 35.05 | 51.54 | 13.41 |
| 2 | 62.00 | 10.00 | 6 | 45.60 | 45.44 | 8.96 |
|  |  |  | 8 | 39.81 | 49.41 | 10.78 |
| 3 | 67.00 | 8.00 | 6 | 54.89 | 40.25 | 4.86 |
|  |  |  | 8 | 50.81 | 43.18 | 6.02 |
| 4 | 57.00 | 8.00 | 6 | 56.22 | 38.94 | 4.83 |
|  |  |  | 8 | 49.40 | 45.05 | 5.55 |
| 5 | 54.93 | 10.00 | 6 | 60.02 | 34.31 | 5.67 |
|  |  |  | 8 | 51.25 | 42.41 | 6.33 |
| 6 | 62.00 | 10.00 | 6 | 45.43 | 47.77 | 6.80 |
|  |  |  | 8 | 39.39 | 51.07 | 9.54 |
| 7 | 69.07 | 10.00 | 6 | 53.55 | 42.39 | 4.06 |
|  |  |  | 8 | 50.69 | 44.47 | 4.84 |
| 8 | 62.00 | 7.17 | 6 | 54.71 | 41.10 | 4.19 |
|  |  |  | 8 | 48.24 | 45.70 | 6.06 |
| 9 | 57.00 | 12.00 | 6 | 43.51 | 49.91 | 6.58 |
|  |  |  | 8 | 36.72 | 53.63 | 9.65 |
| 10 | 67.00 | 12.00 | 6 | 43.79 | 48.42 | 7.79 |
|  |  |  | 8 | 40.80 | 50.06 | 9.14 |
| 11 | 62.00 | 10.00 | 6 | 44.25 | 47.46 | 8.29 |
|  |  |  | 8 | 38.54 | 50.99 | 10.47 |

Results

The culture volume in the bioreactors was harvested after 94 hrs and the biomass separated from the volume. The enzyme assays of the two strains yielded enzyme activities of 1202 U/ml for *P. pastoris* fopA and 1124 U/ml for G250.2.

Figure 9:
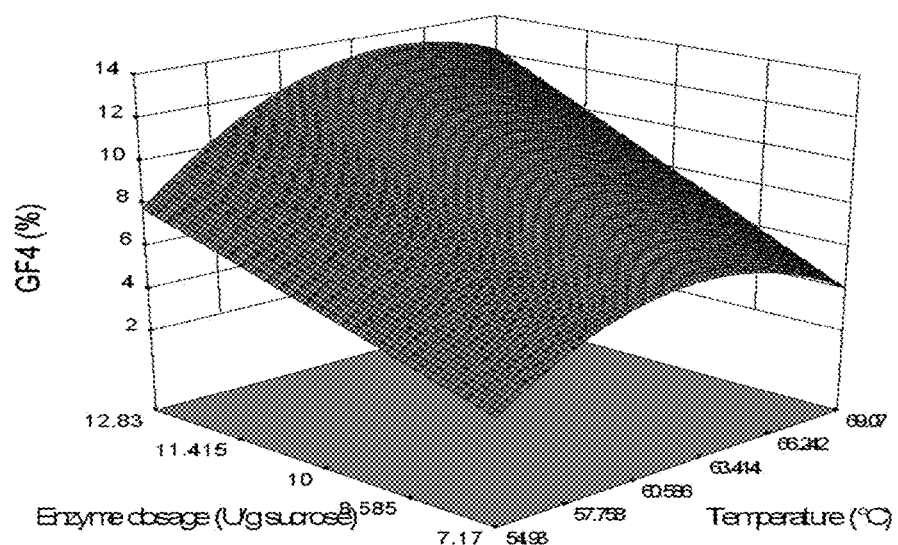
FIG. 9: Response surface plots of GF4 percentage of total scFOS as a function of temperature (A) and enzyme dosage (B) for the enzyme fopA_V1 after 6 hrs.
Figure 10:
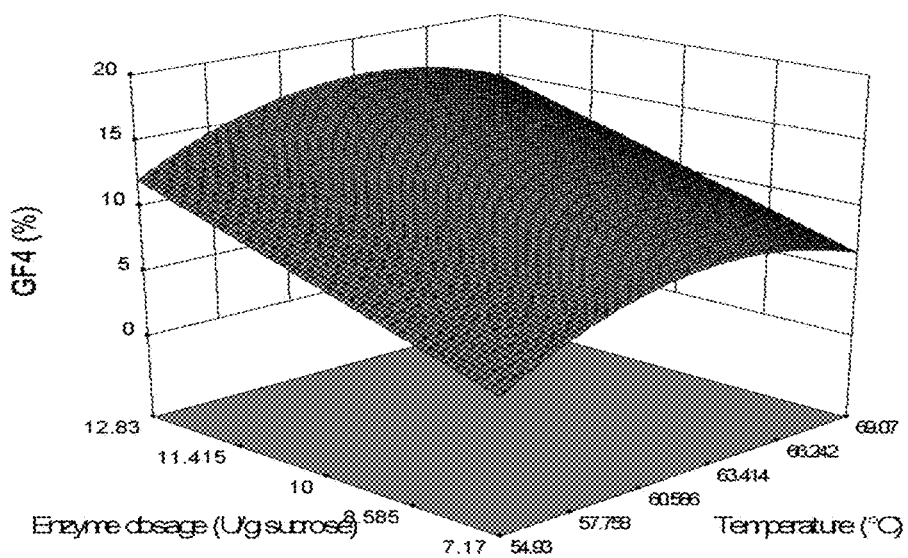
FIG. 10: Response surface plots of GF4 percentage of total scFOS as a function of temperature (A) and enzyme dosage (B) for the enzyme fopA_V1 after 8 hrs.
Figure 11:
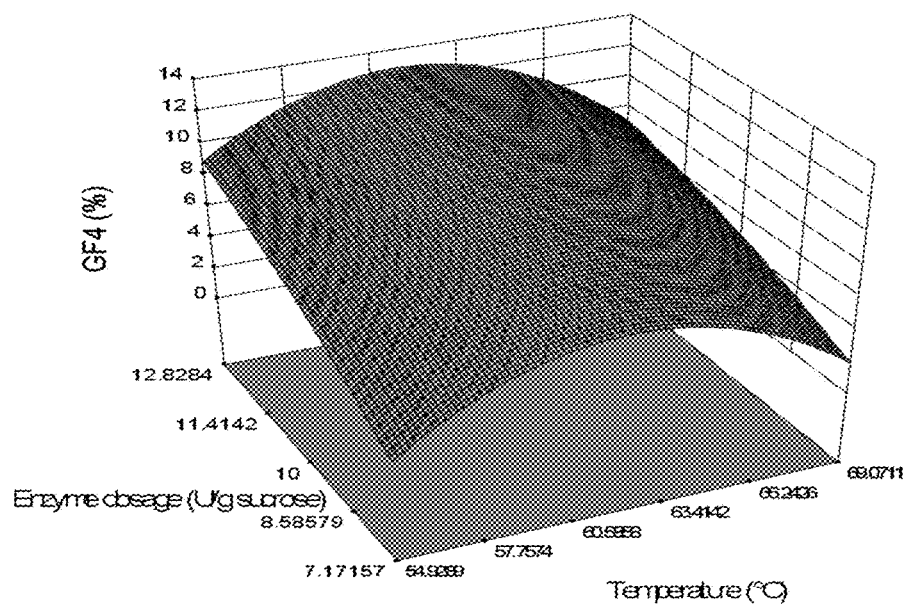
FIG. 11: Response surface plots of GF4 percentage of total scFOS as a function of temperature (A) and enzyme dosage (B) for the enzyme fopA after 8 hrs.

The optimum temperature for both enzymes is at ~62° C. (FIGS. 9 to 11), but fopA_V1 was still able to produce 10.06% GF4 after 8 hrs at 69.07° C. This is more than double that for the fopA enzyme, which only produced 4.84% GF4 after the same amount of time. This would indicate that the fopA_V1 enzyme is more thermotolerant compared to the fopA enzyme. Both these enzymes struggled to produce 10% GF4 at the lower temperatures and required an increased enzyme dosage to achieve this (Tables 3 and 4). At enzyme dosages less than 10.00 U/g sucrose, both these enzymes were unable to produce a sugar composition similar to that of Actilight®. At the higher enzyme dosages of 12.83 U/g sucrose (62° C.) and 12.00 U/g sucrose (67° C.), fopA_V1 was able to produce sugar compositions similar to Actilight® at 6 hrs decreasing the incubation time by 2 hrs compared to fopA (FIG. 10 and Table 3).

Generally, the fopA_V1 enzyme produced higher percentage GF4 or similar amounts in shorter time periods than the fopA enzyme at all the conditions tested. It was also able to tolerate higher temperatures and decrease incubation times at the higher enzyme dosages.

REFERENCES

1. Hidaka H, Eida T, Takizawa T, Tokunahga T, Tashiro Y (1986) Effects of fructo-oligosaccharides on intestinal flora and human health. Bifidobact Microflora 5: 37-50.
2. Roberfroid M B (2007) Inulin-type fructans: functional food ingredients. J Nutr 137: 2493S-2502S. Available: http://www.ncbi.nlm.nih.gov/entrez/query.fcgi?cmd=Retrieve&db=PubMed&dopt=Citation&list_uids=17951492. Accessed 4 Feb. 2014.
3. Sangeetha P T, Ramesh M N, Prapulla S G (2005) Recent trends in the microbial production, analysis and application of Fructooligosaccharides. Trends Food Sci Technol 16: 442-457. Available: http://www.sciencedirect.com/science/article/B6VHY-4GHSGHC-1/1/e35b9e9a9d27ffbbaf7197d399b05bff.
4. Singh R, Singh R (2010) Production of fructooligosaccharides from inulin by endoinulinases and their prebiotic potential. Food Technol Biotechnol 48: 435-450. Available: http://www.researchgate.net/publication/215601814_Production_of_Fructooligosaccharides_from_Inulin_by_Endoinulinases_and_Their_Prebiotic_Potential/file/3deec52662ab8ad548.pdf. Accessed 21 Jul. 2014.
5. Cantarel B L, Coutinho P M, Rancurel C, Bernard T, Lombard V, et al. (2009) The Carbohydrate-Active EnZymes database (CAZy): an expert resource for Glycogenomics. Nucleic Acids Res 37: D233-8. Available: http://www.pubmedcentral.nih.gov/articlerender.fcgi?artid=2686590&tool=pmcentrez&render type=abstract. Accessed 22 May 2013.
6. O'Sullivan C, Tompson F W (1890) LX.—Invertase: a contribution to the history of an enzyme or unorganised ferment. J Chem Soc Trans 57: 834. Available: http://xlink.rsc.org/?DOI=ct8905700834. Accessed 12 Mar. 2014.
7. Chuankhayan P, Hsieh C-Y, Huang Y-C, Hsieh Y-Y, Guan H-H, et al. (2010) Crystal structures of *Aspergillus japonicus* fructosyltransferase complex with donor/acceptor substrates reveal complete subsites in the active site for catalysis. J Biol Chem 285: 23251-23264. Available: http://www.jbc.org/content/early/2010/05/13/jbc.M110.113027.abstract. Accessed 20 Feb. 2014.
8. Alberto F, Bignon J, Sulzenbacher G, Henrissat B, Czjzek M (2004) The three-dimensional structure of invertase (beta-fructosidase) from *Thermotoga maritima*reveals a bimodular arrangement and an evolutionary relationship between retaining and inverting glycosidases. J Biol Chem 279: 18903-18910. Available: http://www.jbc.org/content/279/18/18903.abstract. Accessed 21 May 2013.
9. Alvaro-Benito M, Polo A, González B, Fernández-Lobato M, Sanz-Aparicio J (2010) Structural and kinetic analysis of *Schwanniomyces occidentalis* invertase reveals a new oligomerization pattern and the role of its supplementary domain in substrate binding. J Biol Chem 285: 13930-13941. Available: http://www.pubmedcentral.nih.gov/articlerender.fcgi?artid=2859555&tool=pmcentrez&render type=abstract. Accessed 26 Apr. 2013.
10. Sainz-Polo M A, Ramírez-Escudero M, Lafraya A, González B, Marín-Navarro J, et al. (2013) Three-dimensional structure of *Saccharomyces invertase*: role of a non-catalytic domain in oligomerization and substrate specificity. J Biol Chem 288: 9755-9766. Available: http://www.ncbi.nlm.nih.gov/pubmed/23430743. Accessed 1 Apr. 2014.
11. Koshland D E, Stein S S (1954) Correlation of bond breaking with enzyme specificity; cleavage point of invertase. J Biol Chem 208: 139-148. Available: http://www.ncbi.nlm.nih.gov/pubmed/13174523. Accessed 12 Mar. 2014.
12. Pons T, Naumoff D G, Martinez-Fleites C, Hernández L (2004) Three acidic residues are at the active site of a beta-propeller architecture in glycoside hydrolase families 32,43,62, and 68. Proteins 54: 424-432. Available: http://europepmc.org/abstract/MED/14747991. Accessed 10 Jun. 2014.
13. Edelman J (1956) The formation of oligosaccharides by enzymic transglycosylation. In: Nord FF, editor. Advances in Enzymology. New York: Interscience Publishers, Inc., Vol. XVII. p. 189.
14. Hidaka H, Hirayama M, Sumi N (1988) A fructooligosaccharide-producing enzyme from *Aspergillus niger* ATCC 20611. Agric Biol Chem 52: 1181-1187.
15. Zuccaro A, Götze S, Kneip S, Dersch P, Seibel J (2008) Tailor-made fructooligosaccharides by a combination of substrate and genetic engineering. Chembiochem 9: 143-149. Available: http://www.ncbi.nlm.nih.gov/entrez/query.fcgi?cmd=Retrieve&db=PubMed&dopt=Citation&list_uids=18058889. Accessed 17 Jun. 2014.
16. Cruz R, Cruz V D, Belini M Z, Belote J G, Vieira C R (1998) Production of fructooligosaccharides by the mycelia of *Aspergillus japonicus* immobilized in calcium alginate. Bioresour Technol 65: 139-143. Available: http://www.sciencedirect.com/science/article/pii/S0960852498000054. Accessed 17 Jun. 2014.
17. Yoshikawa J, Amachi S, Shinoyama H, Fujii T (2006) Multiple beta-fructofuranosidases by *Aureobasidium pullulans* DSM2404 and their roles in fructooligosaccharide production. FEMS Microbiol Lett 265: 159-163. Available: http://www.ncbi.nlm.nih.gov/entrez/query.fcgi?cmd=Retrieve&db=PubMed&dopt=Citation&list_uids=17052265.
18. Jung K H, Yun J W, Kang K R, Lim J Y, Lee J H (1989) Mathematical model for enzymatic production of fructooligosaccharides from sucrose. Enzyme Microb Technol 11: 491-494. Available: http://linkinghub.elsevier.com/retrieve/pii/014102298990029X.
19. Nishizawa K, Nakajima M, Nabetani H (2001) Kinetic Study on Transfructosylation by β-Fructofuranosidase from *Aspergillus niger* ATCC 20611 and Availability of a Membrane Reactor for Fructooligosaccharide Production. Food Sci Technol Res 7: 39-44. Available: http://joi.jlc.jst.go.jp/JST.JSTAGE/fstr/7.39?from=CrossRef.

20. Yun J W, Song S K. 1999. Enzymatic production of fructooligosaccharides from sucrose, p 141-151. In Bucke C (ed), Carbohydrate biotechnology protocols. Humana Press, Totowa, N.J.
21. De Abreu M A, Alvaro-Benito M, Plou F J, Fernandez-Lobato M, Alcalde M (2011) Screening β-fructofuranosidases mutant libraries to enhance the transglycosylation rates of β-(2→6) fructooligosaccharides. Comb Chem High Throughput Screen 14: 730-738. Available: http://www.ncbi.nlm.nih.gov/pubmed/21599626.
22. Trollope K M, Nieuwoudt H H, Görgens J F, Volschenk H (2014) Screening a random mutagenesis library of a fungal β-fructofuranosidase using FT-MIR ATR spectroscopy and multivariate analysis. Appl Microbiol Biotechnol 98: 4063-4073. Available: http://www.ncbi.nlm.nih.gov/pubmed/24323289. Accessed 21 Jul. 2014.
23. Lafraya Á, Sanz-Aparicio J, Polaina J, Marín-Navarro J (2011) Fructo-oligosaccharide synthesis by mutant versions of Saccharomyces cerevisiae invertase. Appl Environ Microbiol 77: 6148-6157. Available: http://www.pubmedcentral.nih.gov/articlerender.fcgi?artid=3165384&tool=pmcentrez&render type=abstract. Accessed 26 Apr. 2013.
24. Alvaro-Benito M, de Abreu M, Portillo F, Sanz-Aparicio J, Fernández-Lobato M (2010) New insights into the fructosyltransferase activity of Schwanniomyces occidentalis β-fructofuranosidase, emerging from nonconventional codon usage and directed mutation. Appl Environ Microbiol 76: 7491-7499. Available: http://www.pubmedcentral.nih.gov/articlerender.fcgi?artid=2976189&tool=pmcentrez&render type=abstract. Accessed 17 Jun. 2014.
25. Brachmann C B, Davies A, Cost G J, Caputo E, Li J, et al. (1998) Designer deletion strains derived from Saccharomyces cerevisiae S288C: a useful set of strains and plasmids for PCR-mediated gene disruption and other applications. Yeast 14: 115-132. Available: http://www.ncbi.nlm.nih.gov/pubmed/9483801. Accessed 25 Mar. 2014.
26. Wang B-D, Chen D-C, Kuo T-T (2001) Characterization of a Saccharomyces cerevisiae mutant with oversecretion phenotype. Appl Microbiol Biotechnol 55: 712-720. Available: http://link.springer.com/10.1007/s002530100594. Accessed 25 Mar. 2014.
27. Sambrook J, Fritsch E, Maniatis T, editors (1989) Molecular Cloning: A Laboratory Manual. 2nd ed. Cold Spring Harbor, NY: Cold Spring Harbor Laboratory Press.
28. Saarelainen R, Paloheimo M, Fagerström R, Suominen P, Nevalainen K (1993) Cloning, sequencing and enhanced expression of the Trichoderma reesei endoxylanase II (pl 9) gene xln2. Mol Gen Genet 241: 497-503.
29. Sander C, Schneider R (1994) The HSSP database of protein structure-sequence alignments. Nucleic Acids Res 22: 3597-3599. Available: http://ukpmc.ac.uk/abstract/MED/7937066. Accessed 7 Mar. 2014.
30. Shrake A, Rupley J A (1973) Environment and exposure to solvent of protein atoms. Lysozyme and insulin. J Mol Biol 79: 351-371. Available: http://www.sciencedirect.com/science/article/pii/0022283673900119. Accessed 10 Apr. 2014.
31. Zielenkiewicz P, Saenger W (1992) Residue solvent accessibilities in the unfolded polypeptide chain. Biophys J 63: 1483-1486. Available: http://www.pubmedcentral.nih.gov/articlerender.fcgi?artid=1262262&tool=pmcentrez&render type=abstract.
32. Crous J M, Pretorius I S, van Zyl W H (1995) Cloning and expression of an Aspergillus kawachii endo-1,4-beta-xylanase gene in Saccharomyces cerevisiae. Curr Genet 28: 467-473. Available: http://www.ncbi.nlm.nih.gov/pubmed/8575021. Accessed 26 Apr. 2013.
33. Hill J, Donald K, Griffiths D (1991) DMSO-enhanced whole cell yeast transformation. Nucleic Acids Res 19: 5791. Available: http://nar.oxfordjournals.org/content/19/20/5791.full.pdf. Accessed 31 Jul. 2013.
34. Sherman F, Fink G, Lawrence C (1979) Methods in Yeast Genetics. Cold Spring Harbor, N.Y.: Cold Spring Harbor Laboratory Press.
35. Hirayama M, Sumi N, Hidaka H (1989) Purification and properties of a Fructooligosaccharide-producing beta-fructofuranosidase from Aspergillus niger ATCC 20611. Agric Biol Chem 53: 667-673.
36. Gallagher S R, Sasse J (2012) Staining Proteins in Gels. Current Protocols Essential Laboratory Techniques. John Wiley & Sons, Inc. pp. 6:7.4:7.4.1-7.4.14. Available: http://dx.doi.org/10.1002/9780470089941.et0704s06.
37. Niesen F H, Berglund H, Vedadi M (2007) The use of differential scanning fluorimetry to detect ligand interactions that promote protein stability. Nat Protoc 2: 2212-2221. Available: http://www.ncbi.nlm.nih.gov/pubmed/17853878. Accessed 11 Aug. 2013.
38. Arnold K, Bordoli L, Kopp J, Schwede T (2006) The SWISS-MODEL workspace: a web-based environment for protein structure homology modelling. Bioinforma 22: 195-201. Available: http://bioinformatics.oxfordjournals.org/content/22/2/195.abstract.
39. Chen M M Y, Snow C D, Vizcarra C L, Mayo S L, Arnold F H (2012) Comparison of random mutagenesis and semi-rational designed libraries for improved cytochrome P450 BM3-catalyzed hydroxylation of small alkanes. Protein Eng Des Sel 25: 171-178. Available: http://peds.oxfordjournals.org/content/25/4/171.abstract. Accessed 19 Mar. 2014.
40. Blom N, Sicheritz-Pontén T, Gupta R, Gammeltoft S, Brunak S (2004) Prediction of post-translational glycosylation and phosphorylation of proteins from the amino acid sequence. Proteomics 4: 1633-1649. Available: http://dx.doi.org/10.1002/pmic.200300771.
41. Yanai K, Nakane A, Kawate A, Hirayama M (2001) Molecular cloning and characterization of the fructooligosaccharide-producing beta-fructofuranosidase gene from Aspergillus niger ATCC 20611. Biosci Biotechnol Biochem 65: 766-773. Available: http://www.ncbi.nlm.nih.gov/entrez/query.fcgi?cmd=Retrieve&db=PubMed&dopt=Citation&list_uids=11388451.
42. Epps D E, Sarver R W, Rogers J M, Herberg J T, Tomich P K (2001) The ligand affinity of proteins measured by isothermal denaturation kinetics. Anal Biochem 292: 40-50. Available: http://www.sciencedirect.com/science/article/pii/S000326970195047X. Accessed 10 Mar. 2014.
43. Lo M-C, Aulabaugh A, Jin G, Cowling R, Bard J, et al. (2004) Evaluation of fluorescence-based thermal shift assays for hit identification in drug discovery. Anal Biochem 332: 153-159. Available: http://www.sciencedirect.com/science/article/pii/S0003269704003756. Accessed 30 Jan. 2014.
44. Schellman J A (1997) Temperature, stability, and the hydrophobic interaction. Biophys J 73: 2960-2964. Available: http://www.pubmedcentral.nih.gov/articlerender.fcgi?artid=1181201&tool=pmcentrez&render type=abstract. Accessed 17 Apr. 2014.

45. Privalov P L (1979) Stability of proteins: small globular proteins. Adv Protein Chem 33: 167-241. Available: http://www.ncbi.nlm.nih.gov/pubmed/44431. Accessed 17 Apr. 2014.
46. Zucker F H, Stewart C, dela Rosa J, Kim J, Zhang L, et al. (2010) Prediction of protein crystallization outcome using a hybrid method. J Struct Biol 171: 64-73. Available: http://www.pubmedcentral.nih.gov/articlerender.fcgi?artid=2957526&tool=pmcentrez&rendertype=abstract. Accessed 27 Mar. 2014.
47. Benkert P, Tosatto S C E, Schomburg D (2008) QMEAN: A comprehensive scoring function for model quality assessment. Proteins 71: 261-277. Available: http://www.ncbi.nlm.nih.gov/pubmed/17932912. Accessed 15 Apr. 2014.
48. Baldwin R L (2007) Energetics of protein folding. J Mol Biol 371: 283-301. Available: http://www.sciencedirect.com/science/article/pii/S0022283607007371. Accessed 28 Mar. 2014.
49. Pace C N, Shirley B A, McNutt M, Gajiwala K (1996) Forces contributing to the conformational stability of proteins. FASEB J 10: 75-83. Available: http://www.ncbi.nlm.nih.gov/pubmed/8566551. Accessed 14 Apr. 2014.
50. Wesson L, Eisenberg D (1992) Atomic solvation parameters applied to molecular dynamics of proteins in solution. Protein Sci 1: 227-235. Available: http://dx.doi.org/10.1002/pro.5560010204. Accessed 16 Apr. 2014.
51. Estrada J, Bernadó P, Blackledge M, Sancho J (2009) ProtSA: a web application for calculating sequence specific protein solvent accessibilies in the unfolded ensemble. BMC Bioinformatics 10: 104-112. Available: http://www.biomedcentral.com/1471-2105/10/104. Accessed 11 Sep. 2014.
52. Betts M J, Russell R B (2003) Amino acid properties and consequences of substitutions. In: Barnes M I, Gray I., editors. Bioinformatics for geneticists. New York: Wiley. Available: http://www.russelllab.org/aas/Val.html.
53. Stites W E, Pranata J (1995) Empirical evaluation of the influence of side chains on the conformational entropy of the polypeptide backbone. Proteins 22: 132-140. Available: http://www.ncbi.nlm.nih.gov/pubmed/7567961. Accessed 4 Apr. 2014.
54. Wallach J (1993) Protein stability and stabilization through protein engineering. Biochem Educ 21: 111. Available: http://linkinghub.elsevier.com/retrieve/pii/0307441293900728. Accessed 4 Apr. 2014.
55. Watanabe K, Masuda T, Ohashi H, Mihara H, Suzuki Y (1994) Multiple Proline Substitutions Cumulatively Thermostabilize Bacillus Cereus ATCC7064 Oligo-1,6-Glucosidase. Eur J Biochem 226: 277-283. Available: http://dx.doi.org/10.1111/j.1432-1033.1994.tb20051.x.
56. Wu I, Arnold F H (2013) Engineered thermostable fungal Cel6A and Cel7A cellobiohydrolases hydrolyze cellulose efficiently at elevated temperatures. Biotechnol Bioeng 110: 1874-1883. Available: http://dx.doi.org/10.1002/bit.24864. Accessed 8 Apr. 2014.
57. Hardy F, Vriend G, Veltman O R, van der Vinne B, Venema G, et al. (1993) Stabilization of Bacillus stearothermophilus neutral protease by introduction of prolines. FEBS Lett 317: 89-92. Available: http://www.sciencedirect.com/science/article/pii/001457939381497N. Accessed 4 Apr. 2014.
58. Schallmey M, Floor R J, Hauer B, Breuer M, Jekel P a, et al. (2013) Biocatalytic and structural properties of a highly engineered halohydrin dehalogenase. Chembiochem 14: 870-881. Available: http://www.ncbi.nlm.nih.gov/pubmed/23585096. Accessed 28 May 2013.
59. Zhang H, Zhang T, Chen K, Shen S, Ruan J, et al. (2009) On the relation between residue flexibility and local solvent accessibility in proteins. Proteins 76: 617-636. Available: http://www.ncbi.nlm.nih.gov/pubmed/19274736. Accessed 8 Apr. 2014.
60. Bujacz A, Jedrzejczak-Krzepkowska M, Bielecki S, Redzynia I, Bujacz G (2011) Crystal structures of the apo form of β-fructofuranosidase from *Bifidobacterium longum* and its complex with fructose. FEBS J 278: 1728-1744. Available: http://dx.doi.org/10.1111/j.1742-4658.2011.08098.x. Accessed 27 Mar. 2014.
61. Saulnier D M a, Molenaar D, de Vos W M, Gibson G R, Kolida S (2007) Identification of prebiotic fructooligosaccharide metabolism in *Lactobacillus plantarum* WCFS1 through microarrays. Appl Environ Microbiol 73: 1753-1765. Available: http://www.pubmedcentral.nih.gov/articlerender.fcgi?artid=1828832&tool=pmcentrez&rendertype=abstract. Accessed 5 Mar. 2013.
62. Molis C, Flourie B, Ouarne F, Gailing M F, Lartigue S, et al. (1996) Digestion, excretion, and energy value of fructooligosaccharides in healthy humans. Am J Clin Nutr 64: 324-328. Available: http://www.ncbi.nlm.nih.gov/entrez/query.fcgi?cmd=Retrieve&db=PubMed&dopt=Citation&list_uids=8780341.
63. Fox R J, Clay M D (2009) Catalytic effectiveness, a measure of enzyme proficiency for industrial applications. Trends Biotechnol 27: 137-140. Available: http://www.ncbi.nlm.nih.gov/pubmed/19193465. Accessed 29 Apr. 2014.
64. Eisenthal R, Danson M J, Hough D W (2007) Catalytic efficiency and kcat/KM: a useful comparator? Trends Biotechnol 25: 247-249. Available: http://www.ncbi.nlm.nih.gov/pubmed/17433847. Accessed 5 Mar. 2013.
65. Yedavalli P, Rao N M (2013) Engineering the loops in a lipase for stability in DMSO. Protein Eng Des Sel 26: 317-324. Available: http://www.ncbi.nlm.nih.gov/pubmed/23404771. Accessed 18 Mar. 2014.
66. Goihberg E, Dym O, Tel-Or S (2007) A single proline substitution is critical for the thermostabilization of *Clostridium beijerinckii* alcohol dehydrogenase. Proteins Struct Funct Bioinforma 204: 196-204. Available: http://onlinelibrary.wiley.com/doi/10.1002/prot.21170/full. Accessed 2 May 2014.
67. Sobolev V, Sorokine A, Prilusky J, Abola E E, Edelman M. 1999. Automated analysis of interatomic contacts in proteins. Bioinformatics 15: 327-332. http://dx.doi.org/10.1093/bioinformatics/15.4.327.
68. Tong W, Wei Y, Murga L F, Ondrechen M J, Williams R J. 2009. Partial Order Optimum Likelihood (POOL): maximum likelihood prediction of protein active site residues using 3D structure and sequence properties. PLoS Comput Biol 5:e1000266. http://dx.doi.org/10.1371/journal.pcbi.1000266.
69. Van Wyk N, Trollope K M, Steenkamp E T, Wingfield B D, Volschenk H. 2013. Identification of the gene for β-fructofuranosidase from *Ceratocystis moniliformis* CMW 10134 and characterization of the enzyme expressed in *Saccharomyces cerevisiae*. BMC Biotechnol. 13:100.

Sequences

SEQ ID No. 1: DNA codon optimised by DNA 2.0 for parent enzyme fopA, including xln2 secretion signal
ATGGTCAGCTTCACTAGTCTGTTGGCTGGAGTTGCAGCTATCTCCGGTGTGCTGGCAGCTCCTGCTGCCGAAG
TAGAGTCTGTAGCAGTGGAAAAGAGATCTTACCACCTAGATACAACAGCCCCTCCTCCAACAAATTTGAGTAC
ACTTCCAAACAATACACTGTTCCATGTTTGGAGGCCAAGAGCACATATTTTGCCAGCCGAAGGTCAAATCGGT
GATCCCTGTGCACACTACACTGACCCATCAACTGGTCTGTTTCATGTTGGATTTTTGCACGACGGTGATGGAA
TTGCAGGAGCCACCACCGCTAATTTGGCTACTTATACGGACACGTCCGACAACGGTTCATTTTTGATTCAACC
CGGTGGCAAAAACGATCCTGTCGCTGTGTTTGACGGTGCAGTTATACCTGTCGGTGTGAATAATACTCCAACG
TTGCTGTATACTTCTGTTAGCTTTTTGCCAATACATTGGTCCATCCCGTACACTCGTGGAAGCGAGACTCAAT
CATTGGCTGTTGCCAGAGATGGTGGTAGAAGATTCGATAAACTGGATCAAGGTCCCGTAATCGCAGATCACCC
ATTTGCAGTGGATGTGACCGCCTTCAGAGATCCTTTTGTTTTCCGTTCGGCTAAGCTAGATGTCCTGTTATCT
CTTGACGAGGAAGTAGCTAGGAATGAAACCGCAGTGCAACAGGCTGTTGACGGATGGACTGAGAAAAATGCTC
CTTGGTACGTGGCCGTATCCGGAGGAGTTCATGGAGTCGGACCCGCACAATTCCTATACAGACAAAATGGTGG
AAATGCAAGCGAGTTCCAATACTGGGAGTATTTGGGAGAATGGTGGCAGGAAGCTACTAATAGTTCATGGGGT
GACGAGGGAACATGGGCTGGCAGATGGGGTTTCAATTTCGAAACAGGAAATGTTGTATTTCTAACTGAGGAAG
GCCACGATCCTCAAACAGGCGAGGTGTTCGTTACTTTGGGTACAGAGGGATCAGGTTTGCCAATTGTTCCCCA
AGTGAGTAGCATTCATGACATGTTGTGGGCAGCTGGTGAAGTTGGTGTTGGTTCCGAGCAGGAAGGCGCCAAA
GTGGAGTTCTCCCCTTCCATGGCTGGTTTCCTTGACTGGGGCTTTTCTGCATACGCAGCCGCTGGTAAAGTTT
TGCCTGCCTCATCCGCAGTTTCTAAGACATCTGGTGTTGAAGTTGACAGATATGTCTCCTTCGTTTGGTTGAC
TGGTGACCAGTATGAGCAAGCTGACGGTTTTCCAACCGCTCAGCAAGGATGGACAGGTTCCTTGTTATTGCCA
CGTGAGCTTAAGGTCCAAACTGTTGAAAACGTGGTTGACAACGAACTGGTGCGTGAAGAGGGTGTTTCCTGGG
TCGTTGGTGAGAGTGATAACCAGACTGCCAGGTTACGAACTTTAGGTATCACTATCGCTAGAGAAACAAAAGC
TGCATTGTTGGCAAACGGTTCCGTGACAGCTGAGGAGGATAGAACCCTACAAACCGCTGCTGTTGTTCCATTC
GCTCAGTCACCATCGTCCAAGTTTTTCGTTTTGACGGCTCAGCTTGAATTTCCTGCTTCTGCTAGATCATCAC
CTCTGCAATCCGGTTTTGAAATTCTCGCTTCGGAATTGGAGAGAACCGCTATCTACTACCAATTTTCTAACGA
AAGCCTAGTGGTTGACCGTTCTCAGACTAGCGCAGCAGCTCCAACTAATCCTGGTCTTGATTCGTTCACAGAA
TCTGGTAAGCTGAGACTTTTCGATGTCATCGAAAATGGTCAAGAGCAAGTCGAGACATTAGACTTGACGGTAG
TGGTAGACAACGCTGTGGTCGAAGTCTATGCTAATGGAAGATTTGCTTTGTCTACTTGGGCCAGGTCATGGTA
TGATAATTCCACACAAATTCGTTTCTTTCATAACGGAGAGGGAGAGGTACAGTTTAGAAATGTTAGCGTTAGT
GAAGGTCTGTACAATGCATGGCCAGAACGTAACTAA SEQ ID No. 2: DNA for parent enzyme fopA (codon-optimised by DNA 2.0), with Geneart ® codon-optimised xln2 secretion signal and his-tagging sequence
ATGGTTTCTTTCACATCCTTGTTGGCTGGTGTTGCTGCTATTTCCGGTGTTTTGGCTGCTCCAGCTGCTGAAG
TTGAATCCGTTGCTGTTGAGAAGAGATCCTACCACTTGGATACTACTGCTCCACCACCAACTAACTTGTCCAC
TTTGCCAAACAACACTTTGTTCCATGTTTGGAGACCAAGAGCACACATTTTGCCAGCTGAGGGTCAAATTGGT
GATCCATGTGCTCACTACACTGACCCATCCACTGGTTTGTTCCACGTTGGTTTCTTGCACGACGGTGATGGTA
TTGCTGGTGCTACTACTGCTAACTTGGCTACTTACACTGACACTTCCGACAACGGTTCCTTCTTGATTCAACC
TGGTGGAAAGAACGATCCAGTTGCTGTTTTCGACGGTGCTGTTATCCCAGTTGGTGTTAACAACACTCCAACT
TTGTTGTACACTTCCGTTTCTTTCTTGCCAATCCACTGGTCCATTCCATACACTAGAGGTTCCGAGACTCAAT
CTTTGGCTGTTGCTAGAGATGGTGGTAGAAGATTCGACAAGTTGGACCAAGGGTCCAGTTATTGCTGATCACCC
ATTCGCTGTTGACGTTACTGCTTTCAGAGATCCATTCGTTTTCAGATCCGCTAAGTTGGACGTTTTGTTGTCC
TTGGACGAGGAAGTTGCTAGAAACGAGACTGCTGTTCAACAAGCTGTTGACGGATGGACTGAAAAGAACGCTC
CTTGGTACGTTGCTGTTTCTGGTGGTGTTCATGGTGTTGGTCCAGCTCAGTTCTTGTACAGACAGAACGGTGG
TAACGCTTCTGAGTTCCAGTACTGGGAATACTTGGGAGAATGGTGGCAAGAGGCTACTAATTCTTCCTGGGGT
GATGAGGGAACTTGGGCTGGTAGATGGGGTTTCAACTTCGAGACTGGTAACGTTTTGTTCTTGACTGAAGAGG
GTCACGATCCACAAACTGGTGAAGTTTTCGTTACTTTGGGTACTGAAGGTTCCGGATTGCCAATTGTTCCTCA
GGTTTCCTCCATTCACGATATGTTGTGGGCTGCTGGTGAAGTTGGTGTTGGTTCTGAACAAGAGGGTGCTAAG
GTTGAGTTCTCTCCATCTATGGCTGGTTTCTTGGACTGGGGATTCTCTGCTTATGCTGCTGCTGGAAAGGTTT
TGCCAGCTTCTTCTGCTGTTTCCAAGACTTCCGGTGTTGAGGTTGACAGATACGTTTCCTTTGTTTGGTTGAC
TGGTGACCAATACGAACAAGCTGACGGTTTTCCAACTGCTCAACAGGGATGGACTGGTTCTTTGTTGTTGCCA
AGAGAGTTGAAGGTTCAGACTGTTGAGAACGTTGTTGACAACGAGCTTGTTAGAGAAGAGGGAGTTTCCTGGG
TTGTCGGTGAATCCGACAATCAGACTGCTAGATTGAGAACTTTGGGTATCACTATCGCTAGAGAGACTAAGGC
TGCTTTGTTGGCTAACGGTTCCGTTACTGCTGAAGAGGACAGAACTTTGCAGACTGCTGCTGTTGTTCCATTC
GCTCAATCTCCATCCTCCAAGTTCTTCGTTTTGACTGCTCAGTTGGAGTTTCCAGCTTCTGCTAGATCCTCTC
CATTGCAATCCGGTTTCGAGATTTTGGCTTCCGAGTTGGAGAGAACTGCTATCTACTACCAGTTCTCCAACGA
GTCTTTGGTTGTTGACAGATCCCAAACTTCTGCTGCTGCTCCAACTAACCCAGGATTGGACTCTTTCACTGAG
TCCGGTAAGTTGAGATTGTTCGACGTTATCGAGAACGGTCAAGAGCAAGTTGAGACTTTGGACTTGACTGTTG
TTGTTGATAACGCTGTTGTTGAGGTTTACGCTAACGGTAGATTCGCTTTGTCTACTTGGGCTAGATCCTGGTA
CGACAACTCCACTCAGATCAGATTCTTCCACAACGGTGAAGGTGAAGTTCAGTTCAGAAACGTTTCCGTTTCC
GAGGGTTTGTACAACGCTTGGCCAGAGAGAAACTAA SEQ ID No. 3: Protein sequence for mature parent enzyme FopA
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVIADHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 4: Variant 1 - F140Y-A178P-G321N-Q490S, crystal structure numbering (F121Y-A159P-G302N-Q471S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV

```
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 5: Variant 2 - F140Y-G321N-Q490S, crystal structure numbering (F121Y-
G302N-Q471S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVIADHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 6: Variant 3 - G321N-F140Y-A178P, crystal structure numbering (G302N-
F121Y-A159P)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWFGSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 7: Variant 4 - G321N-Q490S-A178P, crystal structure numbering (G302N-
Q471S-A159P)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 8: Variant 5 - F140Y-Q490S-A178P, crystal structure numbering (F121Y-
Q471S-A159P)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 9: Variant 6 - G321NF140Y, crystal structure numbering (G302N-F121Y)
SYHLDTTAPPPTNLSTLPNNTLFHVWRPRAHILPAEGQIGDPCAHYTDPSTGLFHVGFLHDGDGIAGAATANL
ATYTDTSDNGSFLIQPGGKNDPVAVFDGAVIPVGVNNTPTLLYTSVSYLPIHWSIPYTRGSETQSLAVARDGG
RRFDKLDQGPVIADHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 10: Variant 7 - G321N-Q490S, crystal structure numbering (G302N-Q471S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVIADHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*
```

Sequences

SEQ ID No. 11: Variant 8 - G321N-A178P, crystal structure numbering (G302N-A159P)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 12: Variant 9 - F140Y-Q490S, crystal structure numbering (F121Y-Q471S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVIADHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 13: Variant 10 - F140Y-A178P, crystal structure numbering (F121Y-A159P)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 14: Variant 11 - Q490S-A178P, crystal structure numbering (Q471S-A159P)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVIPDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 15: Variant 12 - G321N-F140Y-Q490S-A178S, crystal structure numbering (G302N-F121Y-Q471S-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 16: Variant 14 - G321N-F140Y-A178S, crystal structure numbering (G302N-F121Y-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 17: Variant 15 - G321N-Q490S-A178S, crystal structure numbering (G302N-Q471S-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVGSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 18: Variant 16 - F140Y-Q490S-A178S, crystal structure numbering (F121Y-
Q471S-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 19: Variant 19 - G321N-A178S, crystal structure numbering (G302N-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSNLPIVPQVSSIHDMLWAAGEVGVSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 20: Variant 21 - F140Y-A178S, crystal structure numbering (F121Y-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSYLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLQTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 21: Variant 22 - Q490S-A178S, crystal structure numbering (Q471S-A159S)
SYHLDTTAPPPTNLSTLPNNTLFHVWRPRAHILPAEGQIGDPCAHYTDPSTGLFHVGFLHDGDGIAGATTANL
ATYTDTSDNGSFLIQPGGKNDPVAVFDGAVIPVGVNNTPTLLYTSVSFLPIHWSIPYTRGSETQSLAVARDGG
RRFDKLDQGPVISDHPFAVDVTAFRDPFVFRSAKLDVLLSLDEEVARNETAVQQAVDGWTEKNAPWYVAVSGG
VHGVGPAQFLYRQNGGNASEFQYWEYLGEWWQEATNSSWGDEGTWAGRWGFNFETGNVLFLTEEGHDPQTGEV
FVTLGTEGSGLPIVPQVSSIHDMLWAAGEVGVSEQEGAKVEFSPSMAGFLDWGFSAYAAAGKVLPASSAVSK
TSGVEVDRYVSFVWLTGDQYEQADGFPTAQQGWTGSLLLPRELKVQTVENVVDNELVREEGVSWVVGESDNQT
ARLRTLGITIARETKAALLANGSVTAEEDRTLSTAAVVPFAQSPSSKFFVLTAQLEFPASARSSPLQSGFEIL
ASELERTAIYYQFSNESLVVDRSQTSAAAPTNPGLDSFTESGKLRLFDVIENGQEQVETLDLTVVVDNAVVEV
YANGRFALSTWARSWYDNSTQIRFFHNGEGEVQFRNVSVSEGLYNAWPERN*

SEQ ID No. 25: Xln2 secretion signal
MVSFTSLLAGVAAI SGVLAAPAAEVESVAVEKR

SEQ ID No. 26: Protein sequence for parent enzyme FopA including synthetic Xln2
secretion signal
MVSFTSLLAGVAAISGVLAAPAAEVESVAVEKRSYHLDTTAPPPTNLSTLPNNTLFHVWRPRAHILPAEGQIG
DPCAHYTDPSTGLFHVGFLHDGDGIAGATTANLATYTDTSDNGSFLIQPGGKNDPVAVFDGAVIPVGVNNTPT
LLYTSVSFLPIHWSIPYTRGSETQSLAVARDGGRRFDKLDQGPVIADHPFAVDVTAFRDPFVFRSAKLDVLLS
LDEEVARNETAVQQAVDGWTEKNAPWYVAVSGGVHGVGPAQFLYRQNGGNASEFQYWEYLGEWWQEATNSSWG
DEGTWAGRWGFNFETGNVLFLTEEGHDPQTGEVFVTLGTEGSGLPIVPQVSSIHDMLWAAGEVGVSEQEGAK
VEFSPSMAGFLDWGFSAYAAAGKVLPASSAVSKTSGVEVDRYVSFVWLTGDQYEQADGFPTAQQGWTGSLLLP
RELKVQTVENVVDNELVREEGVSWVVGESDNQTARLRTLGITIARETKAALLANGSVTAEEDRTLQTAAVVPF
AQSPSSKFFVLTAQLEFPASARSSPLQSGFEILASELERTAIYYQFSNESLVVDRSQTSAAAPTNPGLDSFTE
SGKLRLFDVIENGQEQVETLDLTVVVDNAVVEVYANGRFALSTWARSWYDNSTQIRFFHNGEGEVQFRNVSVS
EGLYNAWPERN

The invention claimed is:

1. A modified polypeptide having fructofuranosidase activity, wherein the modified polypeptide comprises an amino acid sequence which is at least 90% identical to SEQ ID NO: 3 and which has at least one amino acid substitution including substitution of the alanine (A) at amino acid position 159 of SEQ ID NO: 3.

2. The modified polypeptide according to claim 1, which further includes a secretion signal at its 5' end, the secretion signal having an amino acid sequence which is at least 90% identical to SEQ ID NO: 25, wherein the amino acid sequence of the secretion signal and modified peptide is at least 90% identical to SEQ ID NO: 26.

3. The modified polypeptide according to claim 1, which comprises an amino acid sequence of any one of SEQ ID NOS: 6-8, 11, and 13-21.

4. The modified polypeptide according to claim 1, which comprises amino acid sequence SEQ ID NO: 4.

5. The modified polypeptide according to claim 1, wherein the substitution is an A159P substitution.

6. The modified polypeptide according to claim 1, which further comprises a substitution of:
glycine (G) at position 302 of SEQ ID NO: 3;
glutamine (Q) at position 471 of SEQ ID NO: 3; and/or
phenylalanine (F) at position 121 of SEQ ID NO: 3.

7. The modified polypeptide according to claim 6, wherein the substitution is G302N, Q471S and/or F121Y.

8. The modified polypeptide according to claim 6, which comprises amino acid substitutions at the following positions of SEQ ID NO: 3:
A159-G302.

9. The modified polypeptide according to claim 8, which includes the following modifications:
A159P-G302N.

10. The modified polypeptide according to claim 6, which comprises amino acid substitutions at the following positions of SEQ ID NO: 3:
A159-Q471.

11. The modified polypeptide according to claim 6, which comprises amino acid substitutions at the following positions of SEQ ID NO: 3:
F121-A159.

12. The modified polypeptide according to claim 11, which comprises the following substitutions:
F121Y-A159P.

13. The modified polypeptide according to claim 6, which includes the following modifications:
F121-A159-G302.

14. The modified polypeptide according to claim 13, which includes the following modifications:
F121Y-A159P-G302N.

15. The modified polypeptide according to claim 6, which comprises amino acid substitutions at the following positions of SEQ ID NO: 3:
A159-G302-Q471.

16. The modified polypeptide according to claim 15, which includes the following modifications:
A159P-G302N-Q471S.

17. The modified polypeptide according to claim 6, which includes the following modifications:
F121-A159-Q471.

18. The modified polypeptide according to claim 17, which includes the following modifications:
F121Y-A159P-Q471S.

19. The modified polypeptide according to claim 6, which comprises amino acid substitutions at the following positions of SEQ ID NO: 3:
F121-A159-G302-Q471.

20. The modified polypeptide according to claim 19, which includes the following modifications:
F121Y-A159P-G302N-Q471S.

* * * * *

SEQUENCE LISTING

<160> NUMBER OF SEQ ID NOS: 26

<210> SEQ ID NO 1
<211> LENGTH: 2007
<212> TYPE: DNA
<213> ORGANISM: Aspergillus japonicus

<400> SEQUENCE: 1

```
atggtcagct tcactagtct gttggctgga gttgcagcta tctccggtgt gctggcagct      60
cctgctgccg aagtagagtc tgtagcagtg gaaagagat cttaccacct agatacaaca     120
gcccctcctc aacaaatttt gagtacactt ccaaacaata cactgttcca tgtttggagg    180
ccaagagcac atattttgcc agccgaaggt caaatcggtg atccctgtgc acactacact    240
gacccatcaa ctggtctgtt tcatgttgga ttttttgcacg acggtgatgg aattgcagga   300
gccaccaccg ctaatttggc tacttatacg acacgtccg acaacggttc attttttgatt   360
caacccggtg gcaaaaacga tcctgtcgct gtgtttgacg tgtcagttat acctgtcggt   420
gtgaataata ctccaacgtt gctgtatact tctgttagct ttttgccaat acattggtcc   480
atcccgtaca ctcgtggaag cgagactcaa tcattggctg ttgccagaga tggtggtaga   540
agattcgata aactggatca aggtcccgta atcgcagatc acccatttgc agtggatgtg   600
accgccttca gagatccttt tgttttccgt tcggctaagc tagatgtcct gttatctctt   660
gacgaggaag tagctaggaa tgaaaccgca gtgcaacagg ctgttgacgg atggactgag   720
aaaaatgctc cttggtacgt ggccgtatcc ggaggagttc atggagtcgg acccgcacaa   780
ttcctataca gacaaaatgg tggaaatgca agcgagttcc aatactggga gtatttggga   840
gaatggtggc aggaagctac taatagttca tggggtgacg agggaacatg ggctggcaga   900
tggggtttca atttcgaaac aggaaatgtg ttatttctaa ctgaggaagg ccacgatcct   960
caaacaggcg aggtgttcgt tactttgggt acagagggat caggtttgcc aattgttccc   1020
caagtgagta gcattcatga catgttgtgg gcagctggtg aagttggtgt tggttccgag   1080
caggaaggcg ccaaagtgga gttctcccct tccatggctg gtttccttga ctggggcttt   1140
tctgcatacg cagccgctgg taaagttttg cctgcctcat ccgcagtttc taagacatct   1200
ggtgttgaag ttgacagata tgtctccttc gtttggttga ctggtgacca gtatgagcaa   1260
gctgacggtt ttccaaccgc tcagcaagga tggacaggtt ccttgttatt gccacgtgag   1320
cttaaggtcc aaactgttga aaacgtggtt gacaacgaac tggtgcgtga agagggtgtt   1380
tcctgggtcg ttggtgagag tgataaccag actgccaggt tacgaacttt aggtatcact   1440
atcgctagag aaacaaaagc tgcattgttg gcaaacggtt ccgtgacagc tgaggaggat   1500
agaaccctac aaaccgctgc tgttgttcca ttcgctcagt caccatcgtc caagtttttc   1560
gttttgacgg ctcagcttga atttcctgct tctgctagat catcacctct gcaatccggt   1620
tttgaaattc tcgcttcgga attggagaga accgctatct actaccaatt ttctaacgaa   1680
agcctagtgg ttgaccgttc tcagactagc gcagcagctc caactaatcc tggtcttgat   1740
tcgttcacag aatctggtaa gctgagactt ttcgatgtca tcgaaaatgg tcaagagcaa   1800
gtcgagacat tagacttgac ggtagtggta gacaacgctg tggtcgaagt ctatgctaat   1860
ggaagatttg ctttgtctac ttgggccagg tcatggtatg ataattccac acaaattcgt   1920
ttctttcata acggagaggg agaggtacag tttagaaatg ttagcgttag tgaaggtctg   1980
tacaatgcat ggccagaacg taactaa                                        2007
```

<210> SEQ ID NO 2
<211> LENGTH: 2007
<212> TYPE: DNA
<213> ORGANISM: Aspergillus japonicus

<400> SEQUENCE: 2

| | |
|---|---|
| atggtttctt tcacatcctt gttggctggt gttgctgcta tttccggtgt tttggctgct | 60 |
| ccagctgctg aagttgaatc cgttgctgtt gagaagagat cctaccactt ggatactact | 120 |
| gctccaccac caactaactt gtccactttg ccaaacaaca ctttgttcca tgtttggaga | 180 |
| ccaagagcac acattttgcc agctgagggt caaattggtg atccatgtgc tcactacact | 240 |
| gacccatcca ctggtttgtt tcatgttggt ttcttgcacg acggtgatgg tattgctggt | 300 |
| gctactactg ctaacttggc tacttacact gacacttccg acaacggttc cttcttgatt | 360 |
| caacctggtg aaagaacga tccagttgct gttttcgacg gtgctgttat cccagttggt | 420 |
| gttaacaaca ctccaacttt gttgtacact tccgtttctt tcttgccaat ccactggtcc | 480 |
| attccataca ctagaggttc cgagactcaa tctttggctg ttgctagaga tggtggtaga | 540 |
| agattcgaca gttggacca gggtccagtt attgctgatc acccattcgc tgttgacgtt | 600 |
| actgctttca gagatccatt cgttttcaga tccgctaagt tggacgtttt gttgtccttg | 660 |
| gacgaggaag ttgctagaaa cgagactgct gttcaacaag ctgttgacgg atggactgaa | 720 |
| aagaacgctc cttggtacgt tgctgtttct ggtggtgttc atggtgttgg tccagctcag | 780 |
| ttcttgtaca gacagaacgg tggtaacgct tctgagttcc agtactggga atacttggga | 840 |
| gaatggtggc aagaagctac taattcttcc tggggtgatg agggaacttg gctggtaga | 900 |
| tggggtttca acttcgagac tggtaacgtt ttgttcttga ctgaagaggg tcacgatcca | 960 |
| caaactggtg aagttttcgt actttgggt actgaaggtt ccggattgcc aattgttcct | 1020 |
| caggtttcct ccattcacga tatgttgtgg gctgctggtg aagttggtgt tggttctgaa | 1080 |
| caagagggtg ctaaggttga ttctctcca tctatggctg gtttcttgga ctggggattc | 1140 |
| tctgcttatg ctgctgctgg aaaggttttg ccagcttctt ctgctgtttc caagacttcc | 1200 |
| ggtgttgagg ttgacagata cgtttccttt gtttggttga ctggtgacca atacgaacaa | 1260 |
| gctgacggtt ttccaactgc tcaacaggga tggactggtt cttttgttgt tgccaagagag | 1320 |
| ttgaaggttc agactgttga aacgttgtt gacaacgagc ttgttagaga gagggagtt | 1380 |
| tcctgggttg tcggtgaatc cgacaatcag actgctagat tgagaacttt gggtatcact | 1440 |
| atcgctagag agactaaggc tgcttttgttg gctaacggtt ccgttactgc tgaagaggac | 1500 |
| agaactttgc agactgctgc tgttgttcca ttcgctcaat ctccatcctc caagttcttc | 1560 |
| gttttgactc tcagttgga gtttccagct tctgctagat cctctccatt gcaatccggt | 1620 |
| ttcgagattt tggcttccga gttggagaga actgctatct actaccagtt ctccaacgag | 1680 |
| tctttggttt tgacagatc ccaaacttct gctgctgctc caactaaccc aggattggac | 1740 |
| tcttcactg agtccggtaa gttgagattg ttcgacgtta tcgagaacgg tcaagagcaa | 1800 |
| gttgagactt tggacttgac tgttgttgtt gataacgctg ttgttgaggt ttacgctaac | 1860 |
| ggtagattcg ctttgtctac ttgggctaga tcctggtacg acaactccac tcagatcaga | 1920 |
| ttcttccaca acggtgaagg tgaagttcag ttcagaaacg tttccgtttc cgagggtttg | 1980 |
| tacaacgctt ggccagagag aaactaa | 2007 |

<210> SEQ ID NO 3
<211> LENGTH: 635
<212> TYPE: PRT
<213> ORGANISM: Aspergillus japonicus

<400> SEQUENCE: 3

Ser Tyr His Leu Asp Thr Thr Ala Pro Pro Pro Thr Asn Leu Ser Thr
1               5                   10                  15

-continued

```
Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
        130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Gly Leu Pro
        290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ala Val Ser Lys Thr Ser Gly
        355                 360                 365

Val Glu Val Asp Arg Tyr Val Ser Phe Val Trp Leu Thr Gly Asp Gln
        370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Gly Val Ser Trp Val Val Gly
            420                 425                 430

Glu Ser Asp Asn Gln Thr Ala Arg Leu Arg Thr Leu Gly Ile Thr Ile
```

```
                435                 440                 445
Ala Arg Glu Thr Lys Ala Ala Leu Leu Ala Asn Gly Ser Val Thr Ala
450                 455                 460
Glu Glu Asp Arg Thr Leu Gln Thr Ala Ala Val Val Pro Phe Ala Gln
465                 470                 475                 480
Ser Pro Ser Ser Lys Phe Phe Val Leu Thr Ala Gln Leu Glu Phe Pro
                485                 490                 495
Ala Ser Ala Arg Ser Ser Pro Leu Gln Ser Gly Phe Glu Ile Leu Ala
                500                 505                 510
Ser Glu Leu Glu Arg Thr Ala Ile Tyr Tyr Gln Phe Ser Asn Glu Ser
            515                 520                 525
Leu Val Val Asp Arg Ser Gln Thr Ser Ala Ala Pro Thr Asn Pro
530                 535                 540
Gly Leu Asp Ser Phe Thr Glu Ser Gly Lys Leu Arg Leu Phe Asp Val
545                 550                 555                 560
Ile Glu Asn Gly Gln Glu Val Glu Thr Leu Asp Leu Thr Val Val
                565                 570                 575
Val Asp Asn Ala Val Val Glu Val Tyr Ala Asn Gly Arg Phe Ala Leu
                580                 585                 590
Ser Thr Trp Ala Arg Ser Trp Tyr Asp Asn Ser Thr Gln Ile Arg Phe
            595                 600                 605
Phe His Asn Gly Glu Gly Glu Val Gln Phe Arg Asn Val Ser Val Ser
            610                 615                 620
Glu Gly Leu Tyr Asn Ala Trp Pro Glu Arg Asn
625                 630                 635

<210> SEQ ID NO 4
<211> LENGTH: 635
<212> TYPE: PRT
<213> ORGANISM: Artificial Sequence
<220> FEATURE:
<223> OTHER INFORMATION: Variant of FopA from A. japonicus, with
      F121Y-A159P-G302N-Q471S substitutions

<400> SEQUENCE: 4

Ser Tyr His Leu Asp Thr Thr Ala Pro Pro Thr Asn Leu Ser Thr
1               5                   10                  15
Leu Pro Asn Asn Thr Leu Phe His Val Trp Arg Pro Arg Ala His Ile
                20                  25                  30
Leu Pro Ala Glu Gly Gln Ile Gly Asp Pro Cys Ala His Tyr Thr Asp
            35                  40                  45
Pro Ser Thr Gly Leu Phe His Val Gly Phe Leu His Asp Gly Asp Gly
        50                  55                  60
Ile Ala Gly Ala Thr Thr Ala Asn Leu Ala Thr Tyr Thr Asp Thr Ser
65                  70                  75                  80
Asp Asn Gly Ser Phe Leu Ile Gln Pro Gly Gly Lys Asn Asp Pro Val
                85                  90                  95
Ala Val Phe Asp Gly Ala Val Ile Pro Val Gly Val Asn Asn Thr Pro
            100                 105                 110
Thr Leu Leu Tyr Thr Ser Val Ser Tyr Leu Pro Ile His Trp Ser Ile
        115                 120                 125
Pro Tyr Thr Arg Gly Ser Glu Thr Gln Ser Leu Ala Val Ala Arg Asp
    130                 135                 140
Gly Gly Arg Arg Phe Asp Lys Leu Asp Gln Gly Pro Val Ile Pro Asp
145                 150                 155                 160
```

-continued

```
His Pro Phe Ala Val Asp Val Thr Ala Phe Arg Asp Pro Phe Val Phe
            165                 170                 175

Arg Ser Ala Lys Leu Asp Val Leu Ser Leu Asp Glu Glu Val Ala
        180                 185                 190

Arg Asn Glu Thr Ala Val Gln Gln Ala Val Asp Gly Trp Thr Glu Lys
            195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Asn Leu Pro
    290                 295                 300

Ile Val Pro Gln Val Ser Ser Ile His Asp Met Leu Trp Ala Ala Gly
305                 310                 315                 320

Glu Val Gly Val Gly Ser Glu Gln Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
    450                 455                 460

Glu Glu Asp Arg Thr Leu Ser Thr Ala Ala Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
    530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
```

```
            580                585                590
Ser Thr Trp Ala Arg Ser Trp Tyr Asp Asn Ser Thr Gln Ile Arg Phe
            595                600                605

Phe His Asn Gly Glu Gly Val Gln Phe Arg Asn Val Ser Val Ser
        610                615                620

Glu Gly Leu Tyr Asn Ala Trp Pro Glu Arg Asn
625                630                635

<210> SEQ ID NO 5
<211> LENGTH: 635
<212> TYPE: PRT
<213> ORGANISM: Artificial Sequence
<220> FEATURE:
<223> OTHER INFORMATION: Variant of FopA from A. japonicus, with
      F121Y-G302N-Q471S substitutions

<400> SEQUENCE: 5

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ala Arg Asp
        130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Asn Leu Pro
        290                 295                 300
```

```
Ile Val Pro Gln Val Ser Ser Ile His Asp Met Leu Trp Ala Ala Gly
305                 310                 315                 320

Glu Val Gly Val Gly Ser Glu Gln Gly Ala Lys Val Glu Phe Ser
            325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ala Val Ser Lys Thr Ser Gly
            355                 360                 365

Val Glu Val Asp Arg Tyr Val Ser Phe Val Trp Leu Thr Gly Asp Gln
370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
                420                 425                 430

Glu Ser Asp Asn Gln Thr Ala Arg Leu Arg Thr Leu Gly Ile Thr Ile
                435                 440                 445

Ala Arg Glu Thr Lys Ala Ala Leu Leu Ala Asn Gly Ser Val Thr Ala
450                 455                 460

Glu Glu Asp Arg Thr Leu Ser Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
                500                 505                 510

Ser Glu Leu Glu Arg Thr Ala Ile Tyr Tyr Gln Phe Ser Asn Glu Ser
                515                 520                 525

Leu Val Val Asp Arg Ser Gln Thr Ser Ala Ala Pro Thr Asn Pro
530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
                580                 585                 590

Ser Thr Trp Ala Arg Ser Trp Tyr Asp Asn Ser Thr Gln Ile Arg Phe
            595                 600                 605

Phe His Asn Gly Glu Gly Glu Val Gln Phe Arg Asn Val Ser Val Ser
            610                 615                 620

Glu Gly Leu Tyr Asn Ala Trp Pro Glu Arg Asn
625                 630                 635

<210> SEQ ID NO 6
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-F121Y-A159P substitutions

<400> SEQUENCE: 6

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30
```

```
Leu Pro Ala Glu Gly Gln Ile Gly Asp Pro Cys Ala His Tyr Thr Asp
         35                  40                  45

Pro Ser Thr Gly Leu Phe His Val Gly Phe Leu His Asp Gly Asp Gly
         50                  55                  60

Ile Ala Gly Ala Thr Thr Ala Asn Leu Ala Thr Tyr Thr Asp Thr Ser
 65              70                  75                  80

Asp Asn Gly Ser Phe Leu Ile Gln Pro Gly Gly Lys Asn Asp Pro Val
                 85                  90                  95

Ala Val Phe Asp Gly Ala Val Ile Pro Val Gly Val Asn Asn Thr Pro
             100                 105                 110

Thr Leu Leu Tyr Thr Ser Val Ser Tyr Leu Pro Ile His Trp Ser Ile
             115                 120                 125

Pro Tyr Thr Arg Gly Ser Glu Thr Gln Ser Leu Ala Val Ala Arg Asp
         130                 135                 140

Gly Gly Arg Arg Phe Asp Lys Leu Asp Gln Gly Pro Val Ile Pro Asp
145                 150                 155                 160

His Pro Phe Ala Val Asp Val Thr Ala Phe Arg Asp Pro Phe Val Phe
             165                 170                 175

Arg Ser Ala Lys Leu Asp Val Leu Leu Ser Leu Asp Glu Val Ala
             180                 185                 190

Arg Asn Glu Thr Ala Val Gln Gln Ala Val Asp Gly Trp Thr Glu Lys
         195                 200                 205

Asn Ala Pro Trp Tyr Val Ala Val Ser Gly Gly Val His Gly Val Gly
         210                 215                 220

Pro Ala Gln Phe Leu Tyr Arg Gln Asn Gly Asn Ala Ser Glu Phe
225                 230                 235                 240

Gln Tyr Trp Glu Tyr Leu Gly Glu Trp Gln Glu Ala Thr Asn Ser
                 245                 250                 255

Ser Trp Gly Asp Glu Gly Thr Trp Ala Gly Arg Trp Gly Phe Asn Phe
             260                 265                 270

Glu Thr Gly Asn Val Leu Phe Leu Thr Glu Glu Gly His Asp Pro Gln
         275                 280                 285

Thr Gly Glu Val Phe Val Thr Leu Gly Thr Glu Gly Ser Asn Leu Pro
         290                 295                 300

Ile Val Pro Gln Val Ser Ser Ile His Asp Met Leu Trp Ala Ala Gly
305                 310                 315                 320

Glu Val Gly Val Gly Ser Glu Gln Gly Ala Lys Val Glu Phe Ser
             325                 330                 335

Pro Ser Met Ala Gly Phe Leu Asp Trp Gly Phe Ser Ala Tyr Ala Ala
             340                 345                 350

Ala Gly Lys Val Leu Pro Ala Ser Ser Ala Val Ser Lys Thr Ser Gly
         355                 360                 365

Val Glu Val Asp Arg Tyr Val Ser Phe Val Trp Leu Thr Gly Asp Gln
         370                 375                 380

Tyr Glu Gln Ala Asp Gly Phe Pro Thr Ala Gln Gly Trp Thr Gly
385                 390                 395                 400

Ser Leu Leu Leu Pro Arg Glu Leu Lys Val Gln Thr Val Glu Asn Val
                 405                 410                 415

Val Asp Asn Glu Leu Val Arg Glu Glu Gly Val Ser Trp Val Val Gly
             420                 425                 430

Glu Ser Asp Asn Gln Thr Ala Arg Leu Arg Thr Leu Gly Ile Thr Ile
         435                 440                 445
```

```
Ala Arg Glu Thr Lys Ala Ala Leu Leu Ala Asn Gly Ser Val Thr Ala
    450                 455                 460

Glu Glu Asp Arg Thr Leu Gln Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
530                 535                 540

Gly Leu Asp Ser Phe Thr Glu Ser Gly Lys Leu Arg Leu Phe Asp Val
545                 550                 555                 560

Ile Glu Asn Gly Gln Glu Val Glu Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Val Gln Phe Arg Asn Val Ser Val Ser
    610                 615                 620

Glu Gly Leu Tyr Asn Ala Trp Pro Glu Arg Asn
625                 630                 635
```

<210> SEQ ID NO 7
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-Q471S-A159P substitutions

<400> SEQUENCE: 7

```
Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Pro Asp
145                 150                 155                 160

His Pro Phe Ala Val Asp Val Thr Ala Phe Arg Asp Pro Phe Val Phe
                165                 170                 175
```

```
Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Asn Leu Pro
    290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
    450                 455                 460

Glu Glu Asp Arg Thr Leu Ser Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Ala Pro Thr Asn Pro
    530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
            580                 585                 590
```

-continued

```
Ser Thr Trp Ala Arg Ser Trp Tyr Asp Asn Ser Thr Gln Ile Arg Phe
        595                 600                 605
Phe His Asn Gly Glu Gly Glu Val Gln Phe Arg Asn Val Ser Val Ser
610                 615                 620
Glu Gly Leu Tyr Asn Ala Trp Pro Glu Arg Asn
625                 630                 635

<210> SEQ ID NO 8
<211> LENGTH: 635
<212> TYPE: PRT
<213> ORGANISM: Artificial Sequence
<220> FEATURE:
<223> OTHER INFORMATION: Variant of FopA from A. japonicus, with
      F121Y-Q471S-A159P substitutions

<400> SEQUENCE: 8

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30

Leu Pro Ala Glu Gly Gln Ile Gly Asp Pro Cys Ala His Tyr Thr Asp
        35                  40                  45

Pro Ser Thr Gly Leu Phe His Val Gly Phe Leu His Asp Gly Asp Gly
    50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Pro Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
    210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Gly His Asp Pro Gln
        275                 280                 285

Thr Gly Glu Val Phe Val Thr Leu Gly Thr Glu Gly Ser Gly Leu Pro
    290                 295                 300

Ile Val Pro Gln Val Ser Ser Ile His Asp Met Leu Trp Ala Ala Gly
305                 310                 315                 320
```

```
Glu Val Gly Val Gly Ser Gln Glu Gly Ala Lys Val Glu Phe Ser
            325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
            355                 360                 365

Val Glu Val Asp Arg Tyr Val Ser Phe Val Trp Leu Thr Gly Asp Gln
            370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
            405                 410                 415

Val Asp Asn Glu Leu Val Arg Glu Gly Val Ser Trp Val Val Gly
            420                 425                 430

Glu Ser Asp Asn Gln Thr Ala Arg Leu Arg Thr Leu Gly Ile Thr Ile
            435                 440                 445

Ala Arg Glu Thr Lys Ala Ala Leu Leu Ala Asn Gly Ser Val Thr Ala
            450                 455                 460

Glu Glu Asp Arg Thr Leu Ser Thr Ala Ala Val Val Pro Phe Ala Gln
465                 470                 475                 480

Ser Pro Ser Ser Lys Phe Phe Val Leu Thr Ala Gln Leu Glu Phe Pro
            485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
            515                 520                 525

Leu Val Val Asp Arg Ser Gln Thr Ser Ala Ala Pro Thr Asn Pro
            530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
            565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
            595                 600                 605

Phe His Asn Gly Glu Gly Glu Val Gln Phe Arg Asn Val Ser Val Ser
            610                 615                 620

Glu Gly Leu Tyr Asn Ala Trp Pro Glu Arg Asn
625                 630                 635

<210> SEQ ID NO 9
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-F121Y substitutions

<400> SEQUENCE: 9

Ser Tyr His Leu Asp Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30

Leu Pro Ala Glu Gly Gln Ile Gly Asp Pro Cys Ala His Tyr Thr Asp
```

```
            35                  40                  45
Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ala Arg Asp
        130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Asn Leu Pro
        290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
        370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
        450                 455                 460
```

```
Glu Asp Arg Thr Leu Gln Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
    530                 535                 540

Gly Leu Asp Ser Phe Thr Glu Ser Gly Lys Leu Arg Leu Phe Asp Val
545                 550                 555                 560

Ile Glu Asn Gly Gln Glu Val Glu Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
    610                 615                 620

Glu Gly Leu Tyr Asn Ala Trp Pro Glu Arg Asn
625                 630                 635
```

<210> SEQ ID NO 10
<211> LENGTH: 635
<212> TYPE: PRT
<213> ORGANISM: Artificial Sequence
<220> FEATURE:
<223> OTHER INFORMATION: Variant of FopA from A. japonicus, with G302N-Q471S substitutions

<400> SEQUENCE: 10

```
Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
```

```
            180              185              190
Arg Asn Glu Thr Ala Val Gln Gln Ala Val Asp Gly Trp Thr Glu Lys
            195              200              205
Asn Ala Pro Trp Tyr Val Ala Val Ser Gly Gly Val His Gly Val Gly
            210              215              220
Pro Ala Gln Phe Leu Tyr Arg Gln Asn Gly Asn Ala Ser Glu Phe
225              230              235              240
Gln Tyr Trp Glu Tyr Leu Gly Glu Trp Gln Glu Ala Thr Asn Ser
            245              250              255
Ser Trp Gly Asp Glu Gly Thr Trp Ala Gly Arg Trp Gly Phe Asn Phe
            260              265              270
Glu Thr Gly Asn Val Leu Phe Leu Thr Glu Glu Gly His Asp Pro Gln
            275              280              285
Thr Gly Glu Val Phe Val Thr Leu Gly Thr Glu Gly Ser Asn Leu Pro
            290              295              300
Ile Val Pro Gln Val Ser Ser Ile His Asp Met Leu Trp Ala Ala Gly
305              310              315              320
Glu Val Gly Val Gly Ser Glu Gln Gly Ala Lys Val Glu Phe Ser
            325              330              335
Pro Ser Met Ala Gly Phe Leu Asp Trp Gly Phe Ser Ala Tyr Ala Ala
            340              345              350
Ala Gly Lys Val Leu Pro Ala Ser Ser Ala Val Ser Lys Thr Ser Gly
            355              360              365
Val Glu Val Asp Arg Tyr Val Ser Phe Val Trp Leu Thr Gly Asp Gln
            370              375              380
Tyr Glu Gln Ala Asp Gly Phe Pro Thr Ala Gln Gln Gly Trp Thr Gly
385              390              395              400
Ser Leu Leu Leu Pro Arg Glu Leu Lys Val Gln Thr Val Glu Asn Val
            405              410              415
Val Asp Asn Glu Leu Val Arg Glu Gly Val Ser Trp Val Val Gly
            420              425              430
Glu Ser Asp Asn Gln Thr Ala Arg Leu Arg Thr Leu Gly Ile Thr Ile
            435              440              445
Ala Arg Glu Thr Lys Ala Ala Leu Leu Ala Asn Gly Ser Val Thr Ala
            450              455              460
Glu Glu Asp Arg Thr Leu Ser Thr Ala Ala Val Val Pro Phe Ala Gln
465              470              475              480
Ser Pro Ser Ser Lys Phe Phe Val Leu Thr Ala Gln Leu Glu Phe Pro
            485              490              495
Ala Ser Ala Arg Ser Ser Pro Leu Gln Ser Gly Phe Glu Ile Leu Ala
            500              505              510
Ser Glu Leu Glu Arg Thr Ala Ile Tyr Tyr Gln Phe Ser Asn Glu Ser
            515              520              525
Leu Val Val Asp Arg Ser Gln Thr Ser Ala Ala Pro Thr Asn Pro
            530              535              540
Gly Leu Asp Ser Phe Thr Glu Ser Gly Lys Leu Arg Leu Phe Asp Val
545              550              555              560
Ile Glu Asn Gly Gln Glu Gln Val Glu Thr Leu Asp Leu Thr Val Val
            565              570              575
Val Asp Asn Ala Val Val Glu Val Tyr Ala Asn Gly Arg Phe Ala Leu
            580              585              590
Ser Thr Trp Ala Arg Ser Trp Tyr Asp Asn Ser Thr Gln Ile Arg Phe
            595              600              605
```

```
Phe His Asn Gly Glu Gly Val Gln Phe Arg Asn Val Ser Val Ser
    610                 615                 620

Glu Gly Leu Tyr Asn Ala Trp Pro Glu Arg Asn
625                 630                 635

<210> SEQ ID NO 11
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-A159P substitutions

<400> SEQUENCE: 11

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
    50                  55                  60

Ile Ala Gly Ala Thr Thr Ala Asn Leu Ala Thr Tyr Thr Asp Thr Ser
65              70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
130                 135                 140

Gly Gly Arg Arg Phe Asp Lys Leu Asp Gln Gly Pro Val Ile Pro Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
    210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Gly Ser Asn Leu Pro
    290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
```

```
                        325                 330                 335
Pro Ser Met Ala Gly Phe Leu Asp Trp Gly Phe Ser Ala Tyr Ala Ala
                340                 345                 350
Ala Gly Lys Val Leu Pro Ala Ser Ala Val Ser Lys Thr Ser Gly
            355                 360                 365
Val Glu Val Asp Arg Tyr Val Ser Phe Val Trp Leu Thr Gly Asp Gln
370                 375                 380
Tyr Glu Gln Ala Asp Gly Phe Pro Thr Ala Gln Gln Gly Trp Thr Gly
385                 390                 395                 400
Ser Leu Leu Pro Arg Glu Leu Lys Val Gln Thr Val Glu Asn Val
                405                 410                 415
Val Asp Asn Glu Leu Val Arg Glu Gly Val Ser Trp Val Val Gly
            420                 425                 430
Glu Ser Asp Asn Gln Thr Ala Arg Leu Arg Thr Leu Gly Ile Thr Ile
                435                 440                 445
Ala Arg Glu Thr Lys Ala Ala Leu Leu Ala Asn Gly Ser Val Thr Ala
            450                 455                 460
Glu Glu Asp Arg Thr Leu Gln Thr Ala Ala Val Val Pro Phe Ala Gln
465                 470                 475                 480
Ser Pro Ser Ser Lys Phe Val Leu Thr Ala Gln Leu Glu Phe Pro
                485                 490                 495
Ala Ser Ala Arg Ser Ser Pro Leu Gln Ser Gly Phe Glu Ile Leu Ala
            500                 505                 510
Ser Glu Leu Glu Arg Thr Ala Ile Tyr Tyr Gln Phe Ser Asn Glu Ser
                515                 520                 525
Leu Val Val Asp Arg Ser Gln Thr Ser Ala Ala Pro Thr Asn Pro
            530                 535                 540
Gly Leu Asp Ser Phe Thr Glu Ser Gly Lys Leu Arg Leu Phe Asp Val
545                 550                 555                 560
Ile Glu Asn Gly Gln Glu Gln Val Glu Thr Leu Asp Leu Thr Val Val
                565                 570                 575
Val Asp Asn Ala Val Val Glu Val Tyr Ala Asn Gly Arg Phe Ala Leu
            580                 585                 590
Ser Thr Trp Ala Arg Ser Trp Tyr Asp Asn Ser Thr Gln Ile Arg Phe
            595                 600                 605
Phe His Asn Gly Glu Gly Glu Val Gln Phe Arg Asn Val Ser Val Ser
        610                 615                 620
Glu Gly Leu Tyr Asn Ala Trp Pro Glu Arg Asn
625                 630                 635

<210> SEQ ID NO 12
<211> LENGTH: 635
<212> TYPE: PRT
<213> ORGANISM: Artificial Sequence
<220> FEATURE:
<223> OTHER INFORMATION: Variant of FopA from A. japonicus, with
      (F121Y-Q471S substitutions

<400> SEQUENCE: 12

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30

Leu Pro Ala Glu Gly Gln Ile Gly Asp Pro Cys Ala His Tyr Thr Asp
        35                  40                  45
```

-continued

```
Pro Ser Thr Gly Leu Phe His Val Gly Phe Leu His Asp Gly Asp Gly
    50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Ala Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
    210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Gly Leu Pro
    290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Gly Val Ser Trp Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
    450                 455                 460

Glu Glu Asp Arg Thr Leu Ser Thr Ala Ala Val Val Pro Phe Ala Gln
```

```
                465                 470                 475                 480
        Ser Pro Ser Ser Lys Phe Phe Val Leu Thr Ala Gln Leu Glu Phe Pro
                            485                 490                 495

Ala Ser Ala Arg Ser Ser Pro Leu Gln Ser Gly Phe Glu Ile Leu Ala
                        500                 505                 510

Ser Glu Leu Glu Arg Thr Ala Ile Tyr Tyr Gln Phe Ser Asn Glu Ser
                        515                 520                 525

Leu Val Val Asp Arg Ser Gln Thr Ser Ala Ala Pro Thr Asn Pro
                        530                 535                 540

Gly Leu Asp Ser Phe Thr Glu Ser Gly Lys Leu Arg Leu Phe Asp Val
        545                 550                 555                 560

Ile Glu Asn Gly Gln Glu Val Glu Thr Leu Asp Leu Thr Val Val
                            565                 570                 575

Val Asp Asn Ala Val Val Glu Val Tyr Ala Asn Gly Arg Phe Ala Leu
                        580                 585                 590

Ser Thr Trp Ala Arg Ser Trp Tyr Asp Asn Ser Thr Gln Ile Arg Phe
                    595                 600                 605

Phe His Asn Gly Glu Gly Val Gln Phe Arg Asn Val Ser Val Ser
                    610                 615                 620

Glu Gly Leu Tyr Asn Ala Trp Pro Glu Arg Asn
        625                 630                 635

<210> SEQ ID NO 13
<211> LENGTH: 635
<212> TYPE: PRT
<213> ORGANISM: Artificial Sequence
<220> FEATURE:
<223> OTHER INFORMATION: Variant of FopA from A. japonicus, with
      F121Y-A159P substitutions

<400> SEQUENCE: 13

Ser Tyr His Leu Asp Thr Thr Ala Pro Pro Thr Asn Leu Ser Thr
        1               5                   10                  15

Leu Pro Asn Asn Thr Leu Phe His Val Trp Arg Pro Arg Ala His Ile
                        20                  25                  30

Leu Pro Ala Glu Gly Gln Ile Gly Asp Pro Cys Ala His Tyr Thr Asp
                    35                  40                  45

Pro Ser Thr Gly Leu Phe His Val Gly Phe Leu His Asp Gly Asp Gly
                50                  55                  60

Ile Ala Gly Ala Thr Thr Ala Asn Leu Ala Thr Tyr Thr Asp Thr Ser
        65                  70                  75                  80

Asp Asn Gly Ser Phe Leu Ile Gln Pro Gly Gly Lys Asn Asp Pro Val
                        85                  90                  95

Ala Val Phe Asp Gly Ala Val Ile Pro Val Gly Val Asn Asn Thr Pro
                    100                 105                 110

Thr Leu Leu Tyr Thr Ser Val Ser Tyr Leu Pro Ile His Trp Ser Ile
                    115                 120                 125

Pro Tyr Thr Arg Gly Ser Glu Thr Gln Ser Leu Ala Val Ala Arg Asp
                    130                 135                 140

Gly Gly Arg Arg Phe Asp Lys Leu Asp Gln Gly Pro Val Ile Pro Asp
        145                 150                 155                 160

His Pro Phe Ala Val Asp Val Thr Ala Phe Arg Asp Pro Phe Val Phe
                        165                 170                 175

Arg Ser Ala Lys Leu Asp Val Leu Leu Ser Leu Asp Glu Glu Val Ala
                        180                 185                 190
```

-continued

```
Arg Asn Glu Thr Ala Val Gln Gln Ala Val Asp Gly Thr Glu Lys
        195                 200                 205
Asn Ala Pro Trp Tyr Val Ala Val Ser Gly Gly Val His Gly Val Gly
210                 215                 220
Pro Ala Gln Phe Leu Tyr Arg Gln Asn Gly Gly Asn Ala Ser Glu Phe
225                 230                 235                 240
Gln Tyr Trp Glu Tyr Leu Gly Glu Trp Trp Gln Glu Ala Thr Asn Ser
                245                 250                 255
Ser Trp Gly Asp Glu Gly Thr Trp Ala Gly Arg Trp Gly Phe Asn Phe
            260                 265                 270
Glu Thr Gly Asn Val Leu Phe Leu Thr Glu Glu Gly His Asp Pro Gln
        275                 280                 285
Thr Gly Glu Val Phe Val Thr Leu Gly Thr Glu Gly Ser Gly Leu Pro
    290                 295                 300
Ile Val Pro Gln Val Ser Ser Ile His Asp Met Leu Trp Ala Ala Gly
305                 310                 315                 320
Glu Val Gly Val Gly Ser Glu Gln Glu Gly Ala Lys Val Glu Phe Ser
                325                 330                 335
Pro Ser Met Ala Gly Phe Leu Asp Trp Gly Phe Ser Ala Tyr Ala Ala
            340                 345                 350
Ala Gly Lys Val Leu Pro Ala Ser Ala Val Ser Lys Thr Ser Gly
        355                 360                 365
Val Glu Val Asp Arg Tyr Val Ser Phe Val Trp Leu Thr Gly Asp Gln
    370                 375                 380
Tyr Glu Gln Ala Asp Gly Phe Pro Thr Ala Gln Gln Gly Trp Thr Gly
385                 390                 395                 400
Ser Leu Leu Leu Pro Arg Glu Leu Lys Val Gln Thr Val Glu Asn Val
                405                 410                 415
Val Asp Asn Glu Leu Val Arg Glu Gly Val Ser Trp Val Val Gly
            420                 425                 430
Glu Ser Asp Asn Gln Thr Ala Arg Leu Arg Thr Leu Gly Ile Thr Ile
        435                 440                 445
Ala Arg Glu Thr Lys Ala Ala Leu Leu Ala Asn Gly Ser Val Thr Ala
    450                 455                 460
Glu Glu Asp Arg Thr Leu Gln Thr Ala Ala Val Val Pro Phe Ala Gln
465                 470                 475                 480
Ser Pro Ser Ser Lys Phe Phe Val Leu Thr Ala Gln Leu Glu Phe Pro
                485                 490                 495
Ala Ser Ala Arg Ser Ser Pro Leu Gln Ser Gly Phe Glu Ile Leu Ala
            500                 505                 510
Ser Glu Leu Glu Arg Thr Ala Ile Tyr Tyr Gln Phe Ser Asn Glu Ser
        515                 520                 525
Leu Val Val Asp Arg Ser Gln Thr Ser Ala Ala Pro Thr Asn Pro
    530                 535                 540
Gly Leu Asp Ser Phe Thr Glu Ser Gly Lys Leu Arg Leu Phe Asp Val
545                 550                 555                 560
Ile Glu Asn Gly Gln Glu Gln Val Glu Thr Leu Asp Leu Thr Val Val
                565                 570                 575
Val Asp Asn Ala Val Val Glu Val Tyr Ala Asn Gly Arg Phe Ala Leu
            580                 585                 590
Ser Thr Trp Ala Arg Ser Trp Tyr Asp Asn Ser Thr Gln Ile Arg Phe
        595                 600                 605
Phe His Asn Gly Glu Gly Glu Val Gln Phe Arg Asn Val Ser Val Ser
```

Glu Gly Leu Tyr Asn Ala Trp Pro Glu Arg Asn
625                 630                 635

<210> SEQ ID NO 14
<211> LENGTH: 635
<212> TYPE: PRT
<213> ORGANISM: Artificial Sequence
<220> FEATURE:
<223> OTHER INFORMATION: Variant of FopA from A. japonicus, with
    Q471S-A159P substitutions

<400> SEQUENCE: 14

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30

Leu Pro Ala Glu Gly Gln Ile Gly Asp Pro Cys Ala His Tyr Thr Asp
        35                  40                  45

Pro Ser Thr Gly Leu Phe His Val Gly Phe Leu His Asp Gly Asp Gly
    50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Pro Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
    210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Gly Leu Pro
    290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

```
Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Pro Arg Glu Leu Lys Val Gln Thr Val Glu Asn Val
                405                 410                 415

Val Asp Asn Glu Leu Val Arg Glu Gly Val Ser Trp Val Val Gly
        420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
        450                 455                 460

Glu Glu Asp Arg Thr Leu Ser Thr Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
        500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
        580                 585                 590

Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
        610                 615                 620

Glu Gly Leu Tyr Asn Ala Trp Pro Glu Arg Asn
625                 630                 635

<210> SEQ ID NO 15
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-F121Y-Q471S-A159S substitutions

<400> SEQUENCE: 15

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
        35                  40                  45

Pro Ser Thr Gly Leu Phe His Val Gly Phe Leu His Asp Gly Asp Gly
    50                  55                  60
```

```
Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Asn Leu Pro
    290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
    450                 455                 460

Glu Glu Asp Arg Thr Leu Ser Thr Ala Ala Val Val Pro Phe Ala Gln
465                 470                 475                 480
```

```
Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
    530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Val Gln Phe Arg Asn Val Ser Val Ser
    610                 615                 620

Glu Gly Leu Tyr Asn Ala Trp Pro Glu Arg Asn
625                 630                 635

<210> SEQ ID NO 16
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-F121Y-A159S substitutions

<400> SEQUENCE: 16

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Tyr Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205
```

-continued

```
Asn Ala Pro Trp Tyr Val Ala Val Ser Gly Gly Val His Gly Val Gly
    210                 215                 220
Pro Ala Gln Phe Leu Tyr Arg Gln Asn Gly Gly Asn Ala Ser Glu Phe
225                 230                 235                 240
Gln Tyr Trp Glu Tyr Leu Gly Glu Trp Trp Gln Glu Ala Thr Asn Ser
                    245                 250                 255
Ser Trp Gly Asp Glu Gly Thr Trp Ala Gly Arg Trp Gly Phe Asn Phe
                260                 265                 270
Glu Thr Gly Asn Val Leu Phe Leu Thr Glu Glu Gly His Asp Pro Gln
                275                 280                 285
Thr Gly Glu Val Phe Val Thr Leu Gly Thr Glu Gly Ser Asn Leu Pro
290                 295                 300
Ile Val Pro Gln Val Ser Ser Ile His Asp Met Leu Trp Ala Ala Gly
305                 310                 315                 320
Glu Val Gly Val Gly Ser Glu Gln Gly Ala Lys Val Glu Phe Ser
                325                 330                 335
Pro Ser Met Ala Gly Phe Leu Asp Trp Gly Phe Ser Ala Tyr Ala Ala
                340                 345                 350
Ala Gly Lys Val Leu Pro Ala Ser Ser Ala Val Ser Lys Thr Ser Gly
                355                 360                 365
Val Glu Val Asp Arg Tyr Val Ser Phe Val Trp Leu Thr Gly Asp Gln
                370                 375                 380
Tyr Glu Gln Ala Asp Gly Phe Pro Thr Ala Gln Gln Gly Trp Thr Gly
385                 390                 395                 400
Ser Leu Leu Leu Pro Arg Glu Leu Lys Val Gln Thr Val Glu Asn Val
                405                 410                 415
Val Asp Asn Glu Leu Val Arg Glu Gly Val Ser Trp Val Val Gly
                420                 425                 430
Glu Ser Asp Asn Gln Thr Ala Arg Leu Arg Thr Leu Gly Ile Thr Ile
                435                 440                 445
Ala Arg Glu Thr Lys Ala Ala Leu Leu Ala Asn Gly Ser Val Thr Ala
                450                 455                 460
Glu Glu Asp Arg Thr Leu Gln Thr Ala Ala Val Val Pro Phe Ala Gln
465                 470                 475                 480
Ser Pro Ser Ser Lys Phe Phe Val Leu Thr Ala Gln Leu Glu Phe Pro
                485                 490                 495
Ala Ser Ala Arg Ser Ser Pro Leu Gln Ser Gly Phe Glu Ile Leu Ala
                500                 505                 510
Ser Glu Leu Glu Arg Thr Ala Ile Tyr Tyr Gln Phe Ser Asn Glu Ser
                515                 520                 525
Leu Val Val Asp Arg Ser Gln Thr Ser Ala Ala Pro Thr Asn Pro
                530                 535                 540
Gly Leu Asp Ser Phe Thr Glu Ser Gly Lys Leu Arg Leu Phe Asp Val
545                 550                 555                 560
Ile Glu Asn Gly Gln Glu Val Glu Thr Leu Asp Leu Thr Val Val
                565                 570                 575
Val Asp Asn Ala Val Glu Val Tyr Ala Asn Gly Arg Phe Ala Leu
                580                 585                 590
Ser Thr Trp Ala Arg Ser Trp Tyr Asp Asn Ser Thr Gln Ile Arg Phe
                595                 600                 605
Phe His Asn Gly Glu Gly Glu Val Gln Phe Arg Asn Val Ser Val Ser
610                 615                 620
```

Glu Gly Leu Tyr Asn Ala Trp Pro Glu Arg Asn
625              630              635

<210> SEQ ID NO 17
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-Q471S-A159S substitutions

<400> SEQUENCE: 17

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65              70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Asn Ala Ser Glu Phe
225                 230                 235                 240

Gln Tyr Trp Glu Tyr Leu Gly Glu Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
        275                 280                 285

Thr Gly Glu Val Phe Val Thr Leu Gly Thr Glu Gly Ser Asn Leu Pro
290                 295                 300

Ile Val Pro Gln Val Ser Ser Ile His Asp Met Leu Trp Ala Ala Gly
305                 310                 315                 320

Glu Val Gly Val Gly Ser Glu Gln Gly Ala Lys Val Glu Phe Ser
                325                 330                 335

Pro Ser Met Ala Gly Phe Leu Asp Trp Gly Phe Ser Ala Tyr Ala Ala
            340                 345                 350

```
Ala Gly Lys Val Leu Pro Ala Ser Ser Ala Val Ser Lys Thr Ser Gly
        355                 360                 365

Val Glu Val Asp Arg Tyr Val Ser Phe Val Trp Leu Thr Gly Asp Gln
    370                 375                 380

Tyr Glu Gln Ala Asp Gly Phe Pro Thr Ala Gln Gln Gly Trp Thr Gly
385                 390                 395                 400

Ser Leu Leu Pro Arg Glu Leu Lys Val Gln Thr Val Glu Asn Val
            405                 410                 415

Val Asp Asn Glu Leu Val Arg Glu Glu Gly Val Ser Trp Val Val Gly
        420                 425                 430

Glu Ser Asp Asn Gln Thr Ala Arg Leu Arg Thr Leu Gly Ile Thr Ile
            435                 440                 445

Ala Arg Glu Thr Lys Ala Ala Leu Leu Ala Asn Gly Ser Val Thr Ala
        450                 455                 460

Glu Glu Asp Arg Thr Leu Ser Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
    530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
    610                 615                 620

Glu Gly Leu Tyr Asn Ala Trp Pro Glu Arg Asn
625                 630                 635

<210> SEQ ID NO 18
<211> LENGTH: 635
<212> TYPE: PRT
<213> ORGANISM: Artificial Sequence
<220> FEATURE:
<223> OTHER INFORMATION: Variant of FopA from A. japonicus, with
      F121Y-Q471S-A159S substitutions

<400> SEQUENCE: 18

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30

Leu Pro Ala Glu Gly Gln Ile Gly Asp Pro Cys Ala His Tyr Thr Asp
        35                  40                  45

Pro Ser Thr Gly Leu Phe His Val Gly Phe Leu His Asp Gly Asp Gly
    50                  55                  60

Ile Ala Gly Ala Thr Thr Ala Asn Leu Ala Thr Tyr Thr Asp Thr Ser
```

-continued

```
                65                  70                  75                  80
Asp Asn Gly Ser Phe Leu Ile Gln Pro Gly Lys Asn Asp Pro Val
                    85                  90                  95

Ala Val Phe Asp Gly Ala Val Ile Pro Val Gly Val Asn Asn Thr Pro
                    100                 105                 110

Thr Leu Leu Tyr Thr Ser Val Ser Tyr Leu Pro Ile His Trp Ser Ile
                    115                 120                 125

Pro Tyr Thr Arg Gly Ser Glu Thr Gln Ser Leu Ala Val Ala Arg Asp
                    130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
                    165                 170                 175

Arg Ser Ala Lys Leu Asp Val Leu Leu Ser Leu Asp Glu Glu Val Ala
                    180                 185                 190

Arg Asn Glu Thr Ala Val Gln Gln Ala Val Asp Gly Trp Thr Glu Lys
                    195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Gln Glu Ala Thr Asn Ser
                    245                 250                 255

Ser Trp Gly Asp Glu Gly Thr Trp Ala Gly Arg Trp Gly Phe Asn Phe
                    260                 265                 270

Glu Thr Gly Asn Val Leu Phe Leu Thr Glu Glu Gly His Asp Pro Gln
                    275                 280                 285

Thr Gly Glu Val Phe Val Thr Leu Gly Thr Glu Gly Ser Gly Leu Pro
                    290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                    325                 330                 335

Pro Ser Met Ala Gly Phe Leu Asp Trp Gly Phe Ser Ala Tyr Ala Ala
                    340                 345                 350

Ala Gly Lys Val Leu Pro Ala Ser Ser Ala Val Ser Lys Thr Ser Gly
                    355                 360                 365

Val Glu Val Asp Arg Tyr Val Ser Phe Val Trp Leu Thr Gly Asp Gln
                    370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                    405                 410                 415

Val Asp Asn Glu Leu Val Arg Glu Gly Val Ser Trp Val Val Gly
                    420                 425                 430

Glu Ser Asp Asn Gln Thr Ala Arg Leu Arg Thr Leu Gly Ile Thr Ile
                    435                 440                 445

Ala Arg Glu Thr Lys Ala Ala Leu Leu Ala Asn Gly Ser Val Thr Ala
                    450                 455                 460

Glu Glu Asp Arg Thr Leu Ser Thr Ala Val Val Pro Phe Ala Gln
465                 470                 475                 480

Ser Pro Ser Ser Lys Phe Phe Val Leu Thr Ala Gln Leu Glu Phe Pro
                    485                 490                 495
```

-continued

```
Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
530                 535                 540

Gly Leu Asp Ser Phe Thr Glu Ser Gly Lys Leu Arg Leu Phe Asp Val
545                 550                 555                 560

Ile Glu Asn Gly Gln Glu Val Gly Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
    610                 615                 620

Glu Gly Leu Tyr Asn Ala Trp Pro Glu Arg Asn
625                 630                 635

<210> SEQ ID NO 19
<211> LENGTH: 635
<212> TYPE: PRT
<213> ORGANISM: Artificial Sequence
<220> FEATURE:
<223> OTHER INFORMATION: Variant of FopA from A. japonicus, with
      G302N-A159S substitutions

<400> SEQUENCE: 19

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
            20                  25                  30

Leu Pro Ala Glu Gly Gln Ile Gly Asp Pro Cys Ala His Tyr Thr Asp
        35                  40                  45

Pro Ser Thr Gly Leu Phe His Val Gly Phe Leu His Asp Gly Asp Gly
    50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
        115                 120                 125

Pro Tyr Thr Arg Gly Ser Glu Thr Gln Ser Leu Ala Val Ala Arg Asp
    130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
        195                 200                 205

Asn Ala Pro Trp Tyr Val Ala Val Ser Gly Gly Val His Gly Val Gly
```

```
            210                 215                 220
Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
                260                 265                 270

Glu Thr Gly Asn Val Leu Phe Leu Thr Glu Gly His Asp Pro Gln
                275                 280                 285

Thr Gly Glu Val Phe Val Thr Leu Gly Thr Glu Gly Ser Asn Leu Pro
                290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
                340                 345                 350

Ala Gly Lys Val Leu Pro Ala Ser Ala Val Ser Lys Thr Ser Gly
                355                 360                 365

Val Glu Val Asp Arg Tyr Val Ser Phe Val Trp Leu Thr Gly Asp Gln
                370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
                420                 425                 430

Glu Ser Asp Asn Gln Thr Ala Arg Leu Arg Thr Leu Gly Ile Thr Ile
                435                 440                 445

Ala Arg Glu Thr Lys Ala Ala Leu Leu Ala Asn Gly Ser Val Thr Ala
450                 455                 460

Glu Glu Asp Arg Thr Leu Gln Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
                500                 505                 510

Ser Glu Leu Glu Arg Thr Ala Ile Tyr Tyr Gln Phe Ser Asn Glu Ser
                515                 520                 525

Leu Val Val Asp Arg Ser Gln Thr Ser Ala Ala Pro Thr Asn Pro
                530                 535                 540

Gly Leu Asp Ser Phe Thr Glu Ser Gly Lys Leu Arg Leu Phe Asp Val
545                 550                 555                 560

Ile Glu Asn Gly Gln Glu Gln Val Glu Thr Leu Asp Leu Thr Val Val
                565                 570                 575

Val Asp Asn Ala Val Val Glu Val Tyr Ala Asn Gly Arg Phe Ala Leu
                580                 585                 590

Ser Thr Trp Ala Arg Ser Trp Tyr Asp Asn Ser Thr Gln Ile Arg Phe
                595                 600                 605

Phe His Asn Gly Glu Gly Glu Val Gln Phe Arg Asn Val Ser Val Ser
                610                 615                 620

Glu Gly Leu Tyr Asn Ala Trp Pro Glu Arg Asn
625                 630                 635
```

<210> SEQ ID NO 20
<211> LENGTH: 635
<212> TYPE: PRT
<213> ORGANISM: Artificial Sequence
<220> FEATURE:
<223> OTHER INFORMATION: Variant of FopA from A. japonicus, with F121Y-A159S substitutions

<400> SEQUENCE: 20

```
Ser Tyr His Leu Asp Thr Thr Ala Pro Pro Thr Asn Leu Ser Thr
 1               5                  10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
                35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80

Asp Asn Gly Ser Phe Leu Ile Gln Pro Gly Gly Lys Asn Asp Pro Val
                85                  90                  95

Ala Val Phe Asp Gly Ala Val Ile Pro Val Gly Val Asn Asn Thr Pro
                100                 105                 110

Thr Leu Leu Tyr Thr Ser Val Ser Tyr Leu Pro Ile His Trp Ser Ile
            115                 120                 125

Pro Tyr Thr Arg Gly Ser Glu Thr Gln Ser Leu Ala Val Ala Arg Asp
        130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
                165                 170                 175

Arg Ser Ala Lys Leu Asp Val Leu Leu Ser Leu Asp Glu Glu Val Ala
                180                 185                 190

Arg Asn Glu Thr Ala Val Gln Gln Ala Val Asp Gly Trp Thr Glu Lys
            195                 200                 205

Asn Ala Pro Trp Tyr Val Ala Val Ser Gly Gly Val His Gly Val Gly
        210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
                260                 265                 270

Glu Thr Gly Asn Val Leu Phe Leu Thr Glu Glu Gly His Asp Pro Gln
            275                 280                 285

Thr Gly Glu Val Phe Val Thr Leu Gly Thr Gly Ser Gly Leu Pro
        290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ser Ala Val Ser Lys Thr Ser Gly
```

```
                355                 360                 365
Val Glu Val Asp Arg Tyr Val Ser Phe Val Trp Leu Thr Gly Asp Gln
370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Gly Val Ser Trp Val Val Gly
            420                 425                 430

Glu Ser Asp Asn Gln Thr Ala Arg Leu Arg Thr Leu Gly Ile Thr Ile
        435                 440                 445

Ala Arg Glu Thr Lys Ala Ala Leu Leu Ala Asn Gly Ser Val Thr Ala
    450                 455                 460

Glu Glu Asp Arg Thr Leu Gln Thr Ala Ala Val Val Pro Phe Ala Gln
465                 470                 475                 480

Ser Pro Ser Ser Lys Phe Phe Val Leu Thr Ala Gln Leu Glu Phe Pro
                485                 490                 495

Ala Ser Ala Arg Ser Ser Pro Leu Gln Ser Gly Phe Glu Ile Leu Ala
            500                 505                 510

Ser Glu Leu Glu Arg Thr Ala Ile Tyr Tyr Gln Phe Ser Asn Glu Ser
        515                 520                 525

Leu Val Val Asp Arg Ser Gln Thr Ser Ala Ala Pro Thr Asn Pro
    530                 535                 540

Gly Leu Asp Ser Phe Thr Glu Ser Gly Lys Leu Arg Leu Phe Asp Val
545                 550                 555                 560

Ile Glu Asn Gly Gln Glu Val Glu Thr Leu Asp Leu Thr Val Val
                565                 570                 575

Val Asp Asn Ala Val Val Glu Val Tyr Ala Asn Gly Arg Phe Ala Leu
            580                 585                 590

Ser Thr Trp Ala Arg Ser Trp Tyr Asp Asn Ser Thr Gln Ile Arg Phe
        595                 600                 605

Phe His Asn Gly Glu Gly Glu Val Gln Phe Arg Asn Val Ser Val Ser
    610                 615                 620

Glu Gly Leu Tyr Asn Ala Trp Pro Glu Arg Asn
625                 630                 635

<210> SEQ ID NO 21
<211> LENGTH: 635
<212> TYPE: PRT
<213> ORGANISM: Artificial Sequence
<220> FEATURE:
<223> OTHER INFORMATION: Variant of FopA from A. japonicus, with
      Q471S-A159S substitutions

<400> SEQUENCE: 21

Ser Tyr His Leu Asp Thr Thr Ala Pro Pro Thr Asn Leu Ser Thr
1               5                   10                  15

Leu Pro Asn Asn Thr Leu Phe His Val Trp Arg Pro Arg Ala His Ile
                20                  25                  30

Leu Pro Ala Glu Gly Gln Ile Gly Asp Pro Cys Ala His Tyr Thr Asp
            35                  40                  45

Pro Ser Thr Gly Leu Phe His Val Gly Phe Leu His Asp Gly Asp Gly
        50                  55                  60

Ile Ala Gly Ala Thr Thr Ala Asn Leu Ala Thr Tyr Thr Asp Thr Ser
65                  70                  75                  80
```

```
Asp Asn Gly Ser Phe Leu Ile Gln Pro Gly Lys Asn Asp Pro Val
                85                  90                  95

Ala Val Phe Asp Gly Ala Val Ile Pro Val Gly Val Asn Asn Thr Pro
            100                 105                 110

Thr Leu Leu Tyr Thr Ser Val Ser Phe Leu Pro Ile His Trp Ser Ile
            115                 120                 125

Pro Tyr Thr Arg Gly Ser Glu Thr Gln Ser Leu Ala Val Ala Arg Asp
            130                 135                 140

Gly Gly Arg Arg Phe Asp Lys Leu Asp Gln Gly Pro Val Ile Ser Asp
145                 150                 155                 160

His Pro Phe Ala Val Asp Val Thr Ala Phe Arg Asp Pro Phe Val Phe
            165                 170                 175

Arg Ser Ala Lys Leu Asp Val Leu Leu Ser Leu Asp Glu Glu Val Ala
            180                 185                 190

Arg Asn Glu Thr Ala Val Gln Gln Ala Val Asp Gly Trp Thr Glu Lys
            195                 200                 205

Asn Ala Pro Trp Tyr Val Ala Val Ser Gly Gly Val His Gly Val Gly
210                 215                 220

Pro Ala Gln Phe Leu Tyr Arg Gln Asn Gly Gly Asn Ala Ser Glu Phe
225                 230                 235                 240

Gln Tyr Trp Glu Tyr Leu Gly Glu Trp Trp Gln Glu Ala Thr Asn Ser
                245                 250                 255

Ser Trp Gly Asp Glu Gly Thr Trp Ala Gly Arg Trp Gly Phe Asn Phe
            260                 265                 270

Glu Thr Gly Asn Val Leu Phe Leu Thr Glu Glu Gly His Asp Pro Gln
            275                 280                 285

Thr Gly Glu Val Phe Val Thr Leu Gly Thr Glu Gly Ser Gly Leu Pro
            290                 295                 300

Ile Val Pro Gln Val Ser Ser Ile His Asp Met Leu Trp Ala Ala Gly
305                 310                 315                 320

Glu Val Gly Val Gly Ser Glu Gln Glu Gly Ala Lys Val Glu Phe Ser
                325                 330                 335

Pro Ser Met Ala Gly Phe Leu Asp Trp Gly Phe Ser Ala Tyr Ala Ala
            340                 345                 350

Ala Gly Lys Val Leu Pro Ala Ser Ala Val Ser Lys Thr Ser Gly
            355                 360                 365

Val Glu Val Asp Arg Tyr Val Ser Phe Val Trp Leu Thr Gly Asp Gln
            370                 375                 380

Tyr Glu Gln Ala Asp Gly Phe Pro Thr Ala Gln Gln Gly Trp Thr Gly
385                 390                 395                 400

Ser Leu Leu Leu Pro Arg Glu Leu Lys Val Gln Thr Val Glu Asn Val
                405                 410                 415

Val Asp Asn Glu Leu Val Arg Glu Glu Gly Val Ser Trp Val Val Gly
            420                 425                 430

Glu Ser Asp Asn Gln Thr Ala Arg Leu Arg Thr Leu Gly Ile Thr Ile
            435                 440                 445

Ala Arg Glu Thr Lys Ala Ala Leu Leu Ala Asn Gly Ser Val Thr Ala
            450                 455                 460

Glu Glu Asp Arg Thr Leu Ser Thr Ala Val Val Pro Phe Ala Gln
465                 470                 475                 480

Ser Pro Ser Ser Lys Phe Phe Val Leu Thr Ala Gln Leu Glu Phe Pro
            485                 490                 495

Ala Ser Ala Arg Ser Ser Pro Leu Gln Ser Gly Phe Glu Ile Leu Ala
```

```
                500             505             510
Ser Glu Leu Glu Arg Thr Ala Ile Tyr Tyr Gln Phe Ser Asn Glu Ser
        515                 520                 525
Leu Val Val Asp Arg Ser Gln Thr Ser Ala Ala Pro Thr Asn Pro
        530                 535                 540
Gly Leu Asp Ser Phe Thr Glu Ser Gly Lys Leu Arg Leu Phe Asp Val
545                 550                 555                 560
Ile Glu Asn Gly Gln Glu Gln Val Glu Thr Leu Asp Leu Thr Val Val
                565                 570                 575
Val Asp Asn Ala Val Val Glu Val Tyr Ala Asn Gly Arg Phe Ala Leu
        580                 585                 590
Ser Thr Trp Ala Arg Ser Trp Tyr Asp Asn Ser Thr Gln Ile Arg Phe
        595                 600                 605
Phe His Asn Gly Glu Gly Glu Val Gln Phe Arg Asn Val Ser Val Ser
        610                 615                 620
Glu Gly Leu Tyr Asn Ala Trp Pro Glu Arg Asn
625                 630                 635

<210> SEQ ID NO 22
<211> LENGTH: 25
<212> TYPE: DNA
<213> ORGANISM: Artificial Sequence
<220> FEATURE:
<223> OTHER INFORMATION: Forward primer

<400> SEQUENCE: 22
gtttagtaga acctcgtgaa actta                                      25

<210> SEQ ID NO 23
<211> LENGTH: 26
<212> TYPE: DNA
<213> ORGANISM: Artificial Sequence
<220> FEATURE:
<223> OTHER INFORMATION: Reverse primer

<400> SEQUENCE: 23
acttaaaata cgctgaaccc gaacat                                     26

<210> SEQ ID NO 24
<211> LENGTH: 150
<212> TYPE: DNA
<213> ORGANISM: Artificial Sequence
<220> FEATURE:
<223> OTHER INFORMATION: Artifical construct encoding the xyn2 secretion
      signal, 6 histidine residues and a factor Xa protease cleavage
      site

<400> SEQUENCE: 24
atggtttctt tcacatcctt gttggctggt gttgctgcta tttccggtgt tttggctgct    60
ccagctgctg aagttgaatc cgttgctgtt gagaagagac atcaccatca ccatcacgga   120
tccggctctg atctggtat cgagggaaga                                    150

<210> SEQ ID NO 25
<211> LENGTH: 33
<212> TYPE: PRT
<213> ORGANISM: Artificial Sequence
<220> FEATURE:
<223> OTHER INFORMATION: xyn2 secretion signal

<400> SEQUENCE: 25

Met Val Ser Phe Thr Ser Leu Leu Ala Gly Val Ala Ala Ile Ser Gly
```

```
1               5                   10                  15
Val Leu Ala Ala Pro Ala Ala Glu Val Glu Ser Val Ala Val Glu Lys
            20                  25                  30

Arg

<210> SEQ ID NO 26
<211> LENGTH: 668
<212> TYPE: PRT
<213> ORGANISM: Artificial Sequence
<220> FEATURE:
<223> OTHER INFORMATION: xyn2 secretion signal and FopA polypeptide

<400> SEQUENCE: 26

Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Ser Tyr His Leu Asp Thr Thr Ala Pro Pro Thr Asn Leu Ser
        35                  40                  45

Thr Leu Pro Asn Asn Thr Leu Phe His Val Trp Arg Pro Arg Ala His
50                  55                  60

Ile Leu Pro Ala Glu Gly Gln Ile Gly Asp Pro Cys Ala His Tyr Thr
65                  70                  75                  80

Asp Pro Ser Thr Gly Leu Phe His Val Gly Phe Leu His Asp Gly Asp
                85                  90                  95

Gly Ile Ala Gly Ala Thr Thr Ala Asn Leu Ala Thr Tyr Thr Asp Thr
            100                 105                 110

Ser Asp Asn Gly Ser Phe Leu Ile Gln Pro Gly Gly Lys Asn Asp Pro
        115                 120                 125

Val Ala Val Phe Asp Gly Ala Val Ile Pro Val Gly Val Asn Asn Thr
130                 135                 140

Pro Thr Leu Leu Tyr Thr Ser Val Ser Phe Leu Pro Ile His Trp Ser
145                 150                 155                 160

Ile Pro Tyr Thr Arg Gly Ser Glu Thr Gln Ser Leu Ala Val Ala Arg
                165                 170                 175

Asp Gly Gly Arg Arg Phe Asp Lys Leu Asp Gln Gly Pro Val Ile Ala
            180                 185                 190

Asp His Pro Phe Ala Val Asp Val Thr Ala Phe Arg Asp Pro Phe Val
        195                 200                 205

Phe Arg Ser Ala Lys Leu Asp Val Leu Leu Ser Leu Asp Glu Glu Val
210                 215                 220

Ala Arg Asn Glu Thr Ala Val Gln Gln Ala Val Asp Gly Trp Thr Glu
225                 230                 235                 240

Lys Asn Ala Pro Trp Tyr Val Ala Val Ser Gly Gly Val His Gly Val
                245                 250                 255

Gly Pro Ala Gln Phe Leu Tyr Arg Gln Asn Gly Gly Asn Ala Ser Glu
            260                 265                 270

Phe Gln Tyr Trp Glu Tyr Leu Gly Glu Trp Gln Glu Ala Thr Asn
        275                 280                 285

Ser Ser Trp Gly Asp Glu Gly Thr Trp Ala Gly Arg Trp Gly Phe Asn
290                 295                 300

Phe Glu Thr Gly Asn Val Leu Phe Leu Thr Glu Glu Gly His Asp Pro
305                 310                 315                 320
```

```
Gln Thr Gly Glu Val Phe Val Thr Leu Gly Thr Gly Ser Gly Leu
            325                 330             335

Pro Ile Val Pro Gln Val Ser Ser Ile His Asp Met Leu Trp Ala Ala
            340                 345             350

Gly Glu Val Gly Val Gly Ser Glu Gln Glu Gly Ala Lys Val Glu Phe
            355                 360             365

Ser Pro Ser Met Ala Gly Phe Leu Asp Trp Gly Phe Ser Ala Tyr Ala
    370                 375             380

Ala Ala Gly Lys Val Leu Pro Ala Ser Ser Ala Val Ser Lys Thr Ser
385                 390                 395                 400

Gly Val Glu Val Asp Arg Tyr Val Ser Phe Val Trp Leu Thr Gly Asp
                405                 410             415

Gln Tyr Glu Gln Ala Asp Gly Phe Pro Thr Ala Gln Gln Gly Trp Thr
            420                 425             430

Gly Ser Leu Leu Leu Pro Arg Glu Leu Lys Val Gln Thr Val Glu Asn
            435                 440             445

Val Val Asp Asn Glu Leu Val Arg Glu Glu Gly Val Ser Trp Val Val
        450                 455             460

Gly Glu Ser Asp Asn Gln Thr Ala Arg Leu Arg Thr Leu Gly Ile Thr
465                 470             475                 480

Ile Ala Arg Glu Thr Lys Ala Ala Leu Leu Ala Asn Gly Ser Val Thr
                485                 490             495

Ala Glu Glu Asp Arg Thr Leu Gln Thr Ala Ala Val Val Pro Phe Ala
            500             505                 510

Gln Ser Pro Ser Ser Lys Phe Phe Val Leu Thr Ala Gln Leu Glu Phe
        515             520                 525

Pro Ala Ser Ala Arg Ser Ser Pro Leu Gln Ser Gly Phe Glu Ile Leu
    530             535                 540

Ala Ser Glu Leu Glu Arg Thr Ala Ile Tyr Tyr Gln Phe Ser Asn Glu
545             550                 555                 560

Ser Leu Val Val Asp Arg Ser Gln Thr Ser Ala Ala Ala Pro Thr Asn
                565             570                 575

Pro Gly Leu Asp Ser Phe Thr Glu Ser Gly Lys Leu Arg Leu Phe Asp
            580                 585             590

Val Ile Glu Asn Gly Gln Glu Gln Val Glu Thr Leu Asp Leu Thr Val
        595                 600             605

Val Val Asp Asn Ala Val Val Glu Val Tyr Ala Asn Gly Arg Phe Ala
        610             615                 620

Leu Ser Thr Trp Ala Arg Ser Trp Tyr Asp Asn Ser Thr Gln Ile Arg
625                 630             635                 640

Phe Phe His Asn Gly Glu Gly Val Gln Phe Arg Asn Val Ser Val
                645             650                 655

Ser Glu Gly Leu Tyr Asn Ala Trp Pro Glu Arg Asn
            660             665
```